US006936008B2

(12) United States Patent
Tarakci et al.

(10) Patent No.: US 6,936,008 B2
(45) Date of Patent: Aug. 30, 2005

(54) ULTRASOUND SYSTEM WITH CABLELESS COUPLING ASSEMBLY

(75) Inventors: Umit Tarakci, Hayward, CA (US); Mir A. Imran, Los Altos Hills, CA (US); Glen McLaughlin, Saratoga, CA (US); Xufeng Xi, Mountain View, CA (US)

(73) Assignee: Zonare Medical Systems, Inc., Mountain View, CA (US)

( * ) Notice: Subject to any disclaimer, the term of this patent is extended or adjusted under 35 U.S.C. 154(b) by 144 days.

(21) Appl. No.: 10/039,910

(22) Filed: Oct. 20, 2001

(65) Prior Publication Data

US 2002/0138002 A1 Sep. 26, 2002

Related U.S. Application Data

(63) Continuation-in-part of application No. 09/860,209, filed on May 18, 2001, now Pat. No. 6,569,102, which is a continuation of application No. 09/378,175, filed on Aug. 20, 1999, now Pat. No. 6,251,073.

(51) Int. Cl.$^7$ ................................................. A61B 8/00
(52) U.S. Cl. ...................................... 600/437; 600/459
(58) Field of Search ................................. 600/437, 443, 600/447, 459; 73/625, 626; 310/334–336, 367; 29/25.35

(56) References Cited

U.S. PATENT DOCUMENTS

| | | |
|---|---|---|
| 4,409,982 A | 10/1983 | Plesset et al. |
| 4,803,990 A | 2/1989 | Bonnefous et al. |
| 4,853,904 A | 8/1989 | Pesque |
| 4,917,097 A * | 4/1990 | Proudian et al. ............ 600/463 |
| 5,119,342 A | 6/1992 | Harrison, Jr. et al. |
| 5,140,558 A | 8/1992 | Harrison, Jr. et al. |
| 5,267,221 A * | 11/1993 | Miller et al. ................ 367/140 |
| 5,278,757 A | 1/1994 | Hoctor et al. |
| 5,291,090 A | 3/1994 | Dias |
| 5,295,485 A | 3/1994 | Shinomura et al. |
| 5,329,498 A * | 7/1994 | Greenstein ................... 367/155 |
| 5,483,963 A | 1/1996 | Butler et al. |
| 5,505,203 A | 4/1996 | Deitrich et al. |

(Continued)

OTHER PUBLICATIONS

Intermec Technologies Corporation, Intermec Technical Glossary ("ribbon cable") http://home.intermec.com/eprise/main/Intermec/Content/About/Glossary (accessed Jan. 14, 2005).

University of Oxford, Oxford Physics, "Flexible Ribbon Cable," http://www.physics.ox.ac.uk/electronics/pfu/ribbon–htm.htm (accessed Jan. 14, 2005).

Tech–Etch, Inc., Flexible Circuits, "Flexible Circuit Photo Gallery," http://www.tech–etch.com/flex/2layer.html (accessed Jan. 14, 2005).

GC Aero Flexible Printed Circuitry, About Flex, http://www.gcaero.com/htm/aboutflex.htm (accessed Jan. 14, 2005).

A. Pesavento et al., "Compression of Ultrasonic RF Data," IEEE Proc. Ultrasonics Symposium, 1997.

K. Rigby, et al., "Real Time Adaptive Imaging," IEEE Ultrasonics Symposium, pp. 1603–1606, 1988.

(Continued)

*Primary Examiner*—Francis J. Jaworski
(74) *Attorney, Agent, or Firm*—Carr & Ferrell LLP

(57) ABSTRACT

An ultrasound imaging device having a cableless coupling for coupling a two-dimensional array of ultrasound transducers to a signal generating and receiving unit such as a motherboard. The coupling includes an acoustically attenuating and electrically conductive structure, which can include posts that are electrically conductive or electrically insulative having a conductor embedded or mounted on the outer surface. There can also be a high density connector allowing coupling and de-coupling the two dimensional array to and from the motherboard.

24 Claims, 17 Drawing Sheets

U.S. PATENT DOCUMENTS

| | | | |
|---|---|---|---|
| 5,541,468 A | | 7/1996 | Frey et al. |
| 5,559,388 A | * | 9/1996 | Lorraine et al. ............ 310/334 |
| 5,590,658 A | | 1/1997 | Chiang et al. |
| 5,617,862 A | | 4/1997 | Cole et al. |
| 5,648,942 A | * | 7/1997 | Kunkel, III ................. 367/176 |
| 5,667,373 A | | 9/1997 | Wright et al. |
| 5,690,114 A | * | 11/1997 | Chiang et al. .............. 600/447 |
| 5,722,412 A | | 3/1998 | Pflugrath et al. |
| 5,738,099 A | | 4/1998 | Chang |
| 5,740,806 A | | 4/1998 | Miller |
| 5,744,898 A | * | 4/1998 | Smith et al. ................ 310/334 |
| 5,782,769 A | | 7/1998 | Hwang et al. |
| 5,793,701 A | | 8/1998 | Wright et al. |
| 5,795,297 A | * | 8/1998 | Daigle ........................ 600/447 |
| 5,817,024 A | | 10/1998 | Ogle et al. |
| 5,839,442 A | | 11/1998 | Chiang et al. |
| 5,851,186 A | | 12/1998 | Wood et al. |
| 5,873,830 A | | 2/1999 | Hossack et al. |
| 5,893,363 A | | 4/1999 | Little et al. |
| 5,897,501 A | | 4/1999 | Wildes et al. |
| 5,904,652 A | | 5/1999 | Gilbert et al. |
| 5,905,692 A | | 5/1999 | Dolazza et al. |
| 5,919,138 A | | 7/1999 | Ustuner |
| 5,925,967 A | | 7/1999 | Toda |
| 5,951,479 A | | 9/1999 | Holm et al. |
| 5,957,846 A | * | 9/1999 | Chiang et al. .............. 600/447 |
| 5,964,709 A | | 10/1999 | Chiang et al. |
| 5,970,025 A | | 10/1999 | Cole et al. |
| 5,973,438 A | | 10/1999 | Toda |
| 6,043,590 A | * | 3/2000 | Gilmore .................... 310/367 |
| 6,055,861 A | | 5/2000 | Banta, Jr. et al. |
| 6,063,030 A | | 5/2000 | Vara et al. |
| 6,089,096 A | | 7/2000 | Alexandru |
| 6,113,545 A | | 9/2000 | Chiao et al. |
| 6,126,608 A | | 10/2000 | Kemme et al. |
| 6,135,960 A | | 10/2000 | Holmberg |
| 6,135,961 A | | 10/2000 | Pflugrath et al. |
| 6,138,513 A | * | 10/2000 | Barabash et al. ............. 73/602 |
| 6,139,498 A | | 10/2000 | Katsman et al. |
| 6,174,286 B1 | | 1/2001 | Ramamurthy et al. |
| 6,203,498 B1 | | 3/2001 | Bunce et al. |
| 6,230,043 B1 | | 5/2001 | Johnson |
| 6,238,346 B1 | | 5/2001 | Mason |
| 6,251,073 B1 | | 6/2001 | Imran et al. |
| 6,483,228 B2 | * | 11/2002 | Hashimoto .................. 310/336 |
| 6,524,254 B2 | * | 2/2003 | Erikson ...................... 600/447 |
| 6,546,803 B1 | | 4/2003 | Ptchelintsev et al. |
| 6,551,248 B2 | * | 4/2003 | Miller ........................ 600/459 |
| 6,569,102 B2 | * | 5/2003 | Imran et al. ................ 600/459 |

OTHER PUBLICATIONS

C.M. Fabian, et al., "Development of a Parallel Acquisition System of Ultrasound Research," IEEE Proc. Ultrasonics Symposium, 2001.

C. M. Fabian, "Development of a Parallel Acquisition System for Ultrasound Research," Department of Electrical Eng., University of Virginia, (data unknown), pp. 1–9.

U.S. Appl. No. 09/860,209, filed May 18, 2001, Mir Imran, Miniaturized Ultrasound Apparatus and Method.

U.S. Appl. No. 09/872,541, filed May 31, 2001, Glen McLaughlin, System and Method for Phase Inversion Ultrasonic Imaging.

U.S. Appl. No. 10/039,858, filed Oct. 20, 2001, Umit Tarakci, A System and Method for Acoustic Imaging at Two Focal Lengths with a Single Lens.

U.S. Appl. No. 10/039,862, filed Oct. 20, 2001, Ting–Lan Ji, Simultaneous Multi–Mode and Multi–Band Ultrasonic Imaging.

U.S. Appl. No. 10/039,922, filed Oct. 20, 2001, Xufeng Xi, Block Switching in Ultrasound Imaging.

U.S. Appl. No. 29/147,576, filed Aug. 31, 2001, Ian Felix, Handheld Ultrasonic Display Device.

U.S. Appl. No. 29/147,660, filed Aug. 31, 2001, Ian Felix, Handheld Ultrasonic Display Device with Cover.

U.S. Appl. No. 29/148,421, filed Sep. 19, 2001, Ian Felix, Handheld Ultrasonic Transducer with Curved Bulb Grip.

U.S. Appl. No. 29/148,532, filed Sep. 19, 2001, Ian Felix, Handheld Ultrasonic Transducer with Bulb Grip.

U.S Appl. No. 29/149,730, filed Oct. 15, 2001, Ian Felix, Docking Station.

* cited by examiner

ULTRASOUND SYSTEM WITH CABLELESS COUPLING ASSEMBLY

CROSS-REFERENCE TO RELATED APPLICATIONS

This application is a continuation-in-part application of the U.S. patent application Ser. No. 09/860,209, entitled "Miniaturized Ultrasound Apparatus and Method," filed May 18, 2001 and now U.S. Pat. No. 6,569,102, which is a continuation application of U.S. Pat. application Ser. No. 09/378,175, entitled "Miniaturized Ultrasound Apparatus and Method," filed Aug. 20, 1999 and now U.S. Pat. No. 6,251,073. This application is also related to U.S. patent application Ser. No. 10/211,391, entitled "Broad Beam Imaging," and now U.S. Pat. No. 6,685,245.

BACKGROUND OF THE INVENTION

1. Field of the Invention

The invention is in the field of imaging devices and more particularly in the field of portable high-resolution three-dimensional ultrasonic imaging.

2. Description of Prior Art

Ultrasonic imaging is a frequently used method of analysis. The technique is used to examine a wide range of materials and is especially common in medicine because of its relatively non-invasive nature, low cost, and fast response times. Typically, ultrasonic imaging is accomplished by generating and directing ultrasonic waves into a material under investigation. This ultrasonic imaging uses a set of ultrasound generating transducers and then observing reflections generated at the boundaries of dissimilar materials, such as tissues within a patient, also uses a set of ultrasound receiving transducers. The receiving and generating transducers may be arranged in arrays and are typically different sets of transducers but may differ only in the circuitry to which they are connected. The reflections are converted to electrical signals by the receiving transducers and then processed, using techniques known in the art, to determine the locations of echo sources. The resulting data is displayed using a display device, such as a monitor.

The beam intensity as a function of position may oscillate rather than fall off monotonically as a function of distance from the center of the beam. These oscillations in beam intensity are often called "side lobes." In the prior art, the term "apodisation" refers to the process of affecting the distribution of beam intensity to reduce side lobes. However, in the remainder of this specification the term "apodisation" is used to refer to tailoring the distribution of beam intensity for a desired beam characteristic such as having a Guassian or sinc function distribution of beam intensity (without the side lobes).

Steering refers to changing the direction of a beam. Aperture refers to the size of the transducer or group of transducers being used to transmit or receive an acoustic beam.

The prior art process of producing, receiving, and analyzing an ultrasonic beam is called beam forming. The production of ultrasonic beams optionally includes apodisation, steering, focusing, and aperture. Using a prior art data analysis technique each ultrasonic beam is used to generate a one dimensional set of echolocation data. In a typical implementation, a plurality of ultrasonic beams are used to scan a multi-dimensional volume.

Typically, the ultrasonic signal transmitted into the material under investigation is generated by applying continuous or pulsed electronic signals to a transducer. The transmitted ultrasound is commonly in the range of 40 kHz to 10 MHz. The ultrasonic beam propagates through the material under investigation and reflects off of structures such as boundaries between adjacent tissue layers. As it travels, the ultrasonic energy may be scattered, resonated, attenuated, reflected, or transmitted. A portion of the reflected signals are returned to the transducers and detected as echoes. The detecting transducers convert the echo signals to electronic signals for processing using simple filters and signal averagers. After beam forming, an image scan converter uses the calculated positional information to generate two dimensional data that can be presented as an image. In prior art systems the image formation rate (the frame rate) is limited by at least the return time of an ultrasonic pulse. The pulse return time is the time between the transmission of ultrasound into the media of interest and the detection of the last reflected signals.

As an ultrasonic pulse propagates through a material of interest, additional harmonic frequency components are generated, which are analyzed and associated with the visualization of boundaries, or image contrast agents designed to re-radiate ultrasound at specific harmonic frequencies. Unwanted reflections within the ultrasound device can cause noise and the appearance of artifacts in the image.

One-dimensional acoustic arrays have a depth of focus that is usually determined by a nonadjustable passive acoustic focusing means that is affixed to each transducer. This type of focusing necessitates using different transducers for different applications with different depths of focus.

Two-dimensional transducer arrays used for high-speed three-dimensional imaging applications suffer from sensitivity loss caused by coupling multiple signal transfer and distribution systems to ultrasound systems. Two-dimensional transducers used for high-speed three-dimensional imaging applications must have a large number of pixels for two-dimensional steering capability with high resolution. High numbers of radiating/receiving pixels inevitably result in high electrical impedances per pixel in many types of transducers (e.g., piezoelectric, capacitive Micro ElectroMechanical (MEM) transducers), making high-resolution two-dimensional arrays impractical.

To reduce the impedance, many prior art devices use a limited number of elements, or a one-dimensional array. In typical ultrasound systems, these high impedance elements are driven by a typical coaxial cable bundle carrying as many micro-coaxial cables as the number of pixels, with each micro-coaxial cable usually having 50–75 Ohm impedance. These cables do not directly interconnect to the individual elements of the two-dimensional array. Another level of interconnection in the form of multi-layer Printed Circuit Boards (PCBs) co-fired ceramic boards or multi-layer flexes must transfer the signal to the transducer elements. The transducer elements are grouped into pixels each containing one or more transducer elements. For example, each pixel may contain one transmitting and one receiving transducer element. Systems including cables suffer from drawbacks that include, (1) the large number of required micro-coaxial elements makes the cable bundle unwieldy, and (2) the 50–75 ohm cable impedance cannot efficiently interface with or match the high electrical impedances of the individual transducer elements. These drawbacks result in impractically low sensitivity levels. The use of an additional multilayer transition device to connect from cables to transducer elements, introduces additional capacitive loading and crosstalk.

FIG. 1 shows a prior art ultrasonic imaging device 100, including a system 102, a first connector 104, a cable 106, a second connector 108, and a hand held unit 109, which includes a multilayer structure 110 for transmitting the signal, interposing electrical connector structure (not shown), acoustic elements 114, and pins 116. System 102 may include a systems motherboard. The multilayer structure 110 could be a PCB, co-fired ceramic board, or flex circuits, for example. The interposing electrical connector structure (not shown) could be an interposing media for carrying signals from the multilayer structure 110 to acoustic elements 114. The device of FIG. 1 is bulky and can be difficult to move and manipulate because cable 106 has many wires in it and therefore interferes with movement. Cable 106 also needs to be thick and therefore does not bend easily. Handheld unit 109 has electrical contact pads 116 for individually powering the acoustic elements 114.

SUMMARY OF THE INVENTION

An embodiment of the invention provides a miniaturized ultrasound system generating and receiving unit such as a motherboard with two-dimensional signal addressing capability whereby first connector 104, cable 106, and second connector 108 of the prior art device in FIG. 1 can be eliminated. The system may have a system motherboard coupled via a cableless coupling to a transducer array. In one embodiment, the cableless coupling is also wireless (e.g., using the radio-frequency spectrum for transmitting and receiving data and signals). The system may include a two-dimensional surface interconnection between the transducer array and the signal generation and/or detection system, which eliminates the impractically thick and heavy cable. In one embodiment, the signal generation and/or detection system may be electrically matched to the transducer elements increasing the sensitivity more than were transducer elements not matched to the signal generation and/or detection system. The two-dimensional interconnection on the motherboard may be used without any other two-dimensional interconnection. In another embodiment, the electrical connection to the two-dimensional array elements are made via many flex circuits (e.g., printed circuit patterns using a layer of copper foil over a polymer base allowing for multidimensionality whereby the circuit may move, bend and twist without damage to the conductor), each coming from one row of elements, which may be terminated directly on the motherboard row of pads. Flex circuits should not be confused with ribbon cables (e.g., those cables made of normal, round insulated wires arranged side-by-side and fastened together by a cohesion process to form a flexible ribbon).

The two-dimensional array may perform multiple tasks. The motherboard system and the transducers may be designed to provide a sufficient percentage of the bandwidth for multiple frequency operations. For example, for many ultrasound transducers 100% of the bandwidth is necessary for multiple frequency operations. In an embodiment, the depth of focus is not fixed by the physical construction of the array, but is controlled by the area forming electronics and the system software, by active electrical phasing of the two-dimensional array elements. Alternatively, different transducers for different applications with different depths of focus can be used. Changing from one transducer to another can be facilitated by having a high density connector (i.e., a connector having a high density of connector contact pads, one pad for each transducer element (e.g., pixel) of the two-dimensional array) between the two-dimensional array and the system motherboard.

The invention may provide acoustically attenuating mounting posts with low electrical resistance, for example, and allow the two-dimensional arrays of acoustical elements to have a higher sensitivity than were the posts not present. The height of the posts allows the transducer to be oriented for convenient use even though it is an integral part of the motherboard, an other interconnection device, or an other system for example. The permanent connection with the motherboard requires the design of the transducer to provide sufficient bandwidth for multiple frequency operation.

In one embodiment the two-dimensional array is permanently integrated with the motherboard. The depth of focus of the two-dimensional array is not fixed by the physical construction of the array, but is controlled by the area forming electronics and system software, which determine the active phasing of the two-dimensional array elements. This method of control eliminates the necessity of using different transducers for different applications with different fixed depths of focus and allows one transducer affixed to the motherboard, for example, to perform multiple tasks. In another embodiment of this invention different two-dimensional arrays with different depths of focus, frequency, and other characteristics can be plugged to the system motherboard without an intervening cable via the high density connector.

Broad beam technologies refer to systems and methods that include or take advantage of techniques for generating ultrasound and analyzing detected echoes such that multi-dimensional spatial information obtainable from a single ultrasonic pulse.

Area forming is the process of producing, receiving, and analyzing an ultrasonic beam, that optionally includes apodisation, steering, focusing, and aperture control, where a two dimensional set of echolocation data can be generated using only one ultrasonic beam. Nonetheless, more than one ultrasonic beam may still be used with the area forming even though only one is necessary. Area forming is a process separate and distinct from beam forming. Area forming may yield an area of information one transmit and/or receive cycle, in contrast to beam forming that typically only processes a line of information per transmit and/or receive cycle. Alternatively, beam forming can be used instead of area forming electronics throughout this application.

Volume forming is the process of producing, receiving, and analyzing an ultrasonic beam, that optionally includes apodisation, steering, focusing, and aperture control, where a three dimensional set of echolocation data can be generated using only one ultrasonic beam. Nonetheless, multiple ultrasonic beams may be used although not necessary. Volume forming is a superset of area forming.

Multidimensional forming is the process of producing, receiving, and analyzing an ultrasonic beam, that optionally includes apodisation, steering, focusing, and apertures, wherein a two or more dimensional set of spatial echolocation data can be generated using only one ultrasonic beam. Nonetheless, multiple ultrasonic beams may be used although not necessary. Multidimensional forming optionally includes non-spatial dimensions such as time and velocity.

In the above discussion although the motherboard is specified as the signal generating and receiving unit, it is only by way of example and any signal generating and receiving unit can be used.

DETAILED DESCRIPTION OF THE INVENTION

Figure 1:
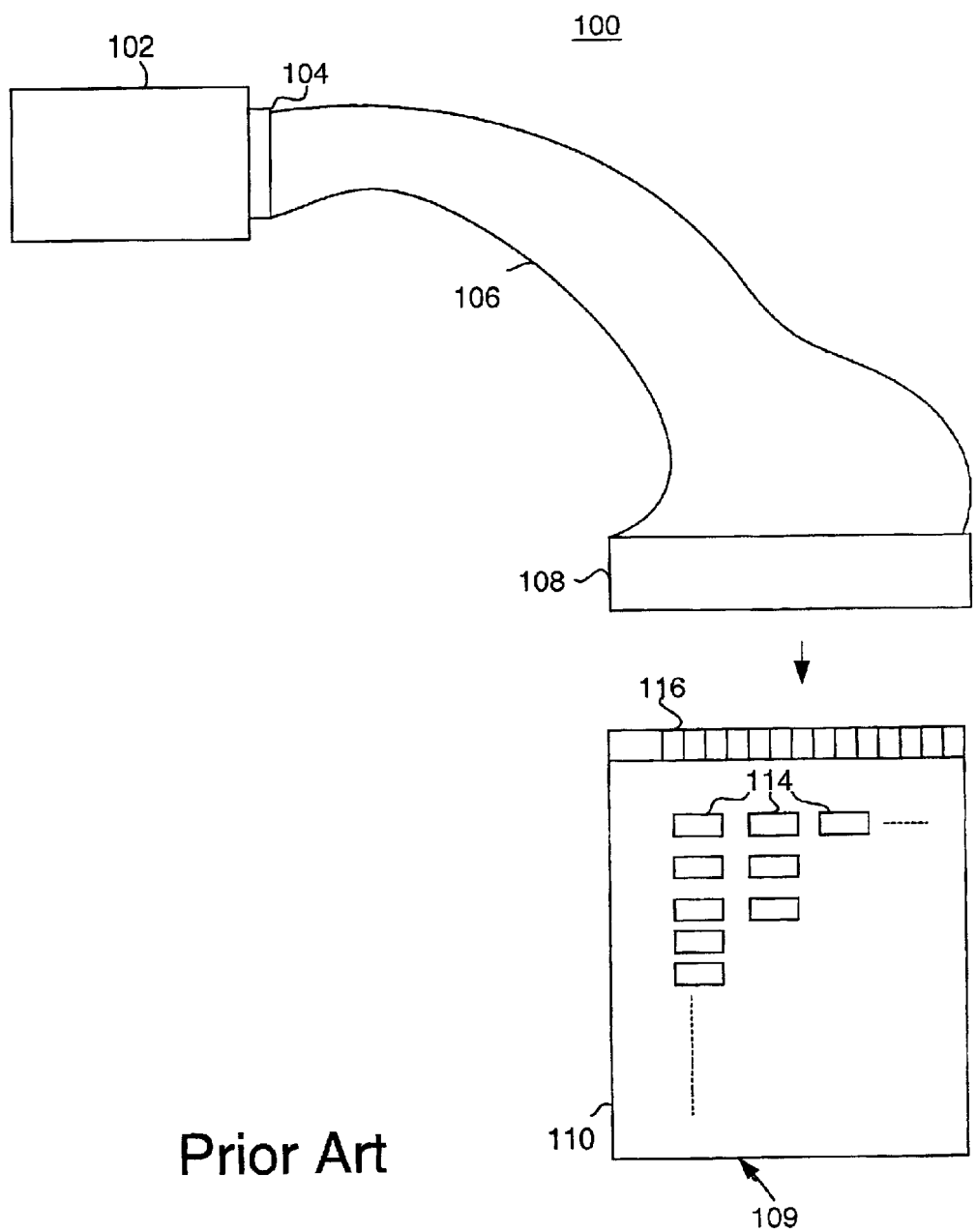
FIG. 1 is a prior art ultrasound device.
Figure 2:
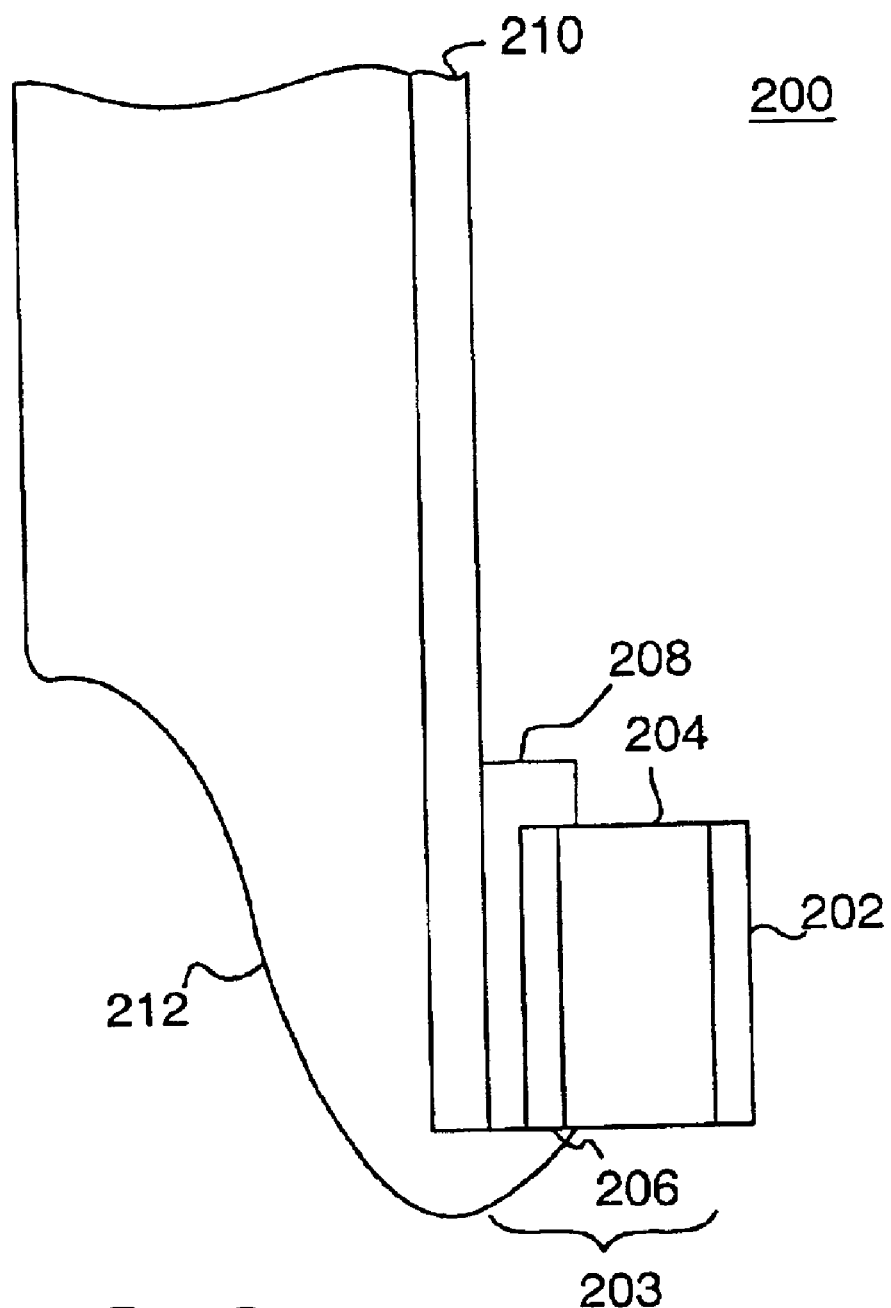
FIG. 2 is an overview of an embodiment of the invention.

FIG. 2 is an overview of one embodiment of the invention. FIG. 2 shows a handheld ultrasound device 200 that includes an ultrasound transducing structure 202 coupled via a cableless coupling 203 to a signal generating and receiving unit 210. The cableless coupling 203 includes an intermediate structure 204, an electrically conducting structure 206, a connector 208. The connector 208 is coupled to the signal generating and receiving unit 210, which are secured within housing 212, and cooperates with cableless coupling 203.

The signals from or to intermediate structure 204 pass through electrically conducting structure 206, connector 208, and the signal generating and receiving unit 210. Ultrasound transducing structure 202 generates, or pulses, in response to signals received via intermediate structure 204, or receives ultrasonic waves and converts them to electrical signals, then sends them to intermediate structure 204.

In an embodiment cableless coupling 203 is also wireless. Signal generating and receiving unit 210 can be an integrated circuit or a system including a motherboard and may also include one or more child boards, for example. Intermediate structure 204 is an electrically coupled and acoustically isolating structure that serves to reduce crosstalk between the elements of the ultrasound transducing structure 202. Additionally, intermediate structure 204 protects ultrasound transducing structure 202 from external or internal acoustical noise and conducts the electrical signal to ultrasound transducing structure 202.

Ultrasound transducing structure 202, intermediate structure 204, and electrically conducting structure 206 may be divided into multiple elements that may be arranged in a periodic lattice. The lattice may be rectangular or hexagonal, for example. Electrically conducting structure 206 may be pads or may be interlocking male and female pins, for example, joining intermediate structure 204 and connector 208. Signal generating and receiving unit 210 may be a system motherboard, for example, and may have a connector 208 that can be a Printed Circuit Board (PCB), co-fired ceramic board, or the like, for signal transmission and distribution. Connector 208 may be a separate component attached to signal generating and receiving unit 210 or may be an integral part of signal generating and receiving unit 210. For example, connector 208 may be a connector region coupled to or on a motherboard. (Throughout this specification the word "on" is to be understood as generic to being an integral part of and to being a separate structure that allows two structures to be attached together. Thus, whenever the specification discusses the connector 208 being "on" signal generating and receiving unit 210 it is to be read as generic to connector 208 being an integral part of and being a separate structure attached to signal generating and receiving unit 210.) Signal generating and receiving unit 210 may include one or more signal processors. The small size of the handheld ultrasound device may allow ultrasound transducing structure 202 to be easily positioned for imaging at a variety of angles.

Alternatively, a section of housing 212 can be made of a flexible material to allow the positioning of the transducer structure 202. Signal generating and receiving unit 210 may be kept small enough and/or may have a section that is made from flexible material to allow handheld ultrasound unit 200 to be flexed, thereby allowing ultrasound transducing structure 202 to be easily positioned for imaging.

Figure 3:
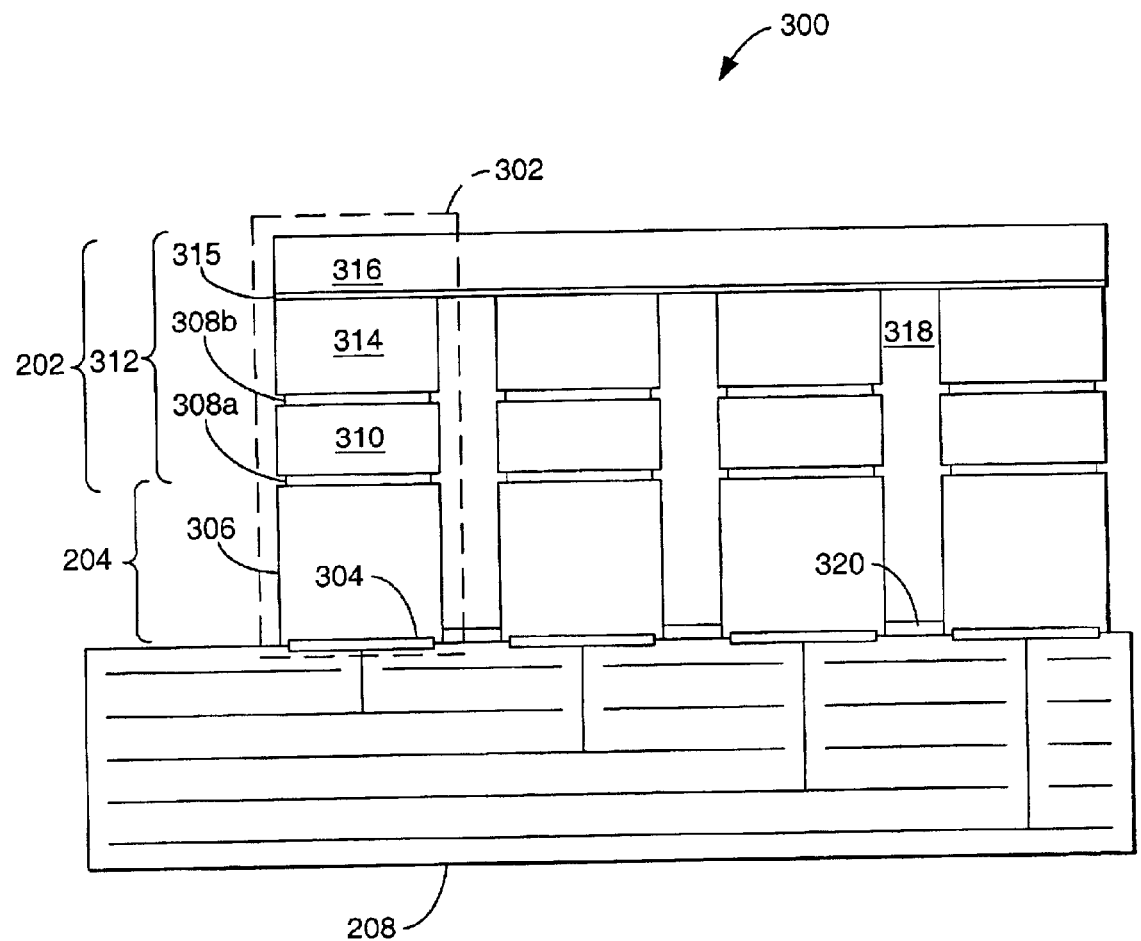
FIG. 3 shows the details of the structure of FIG. 2 according to an embodiment of the invention.

FIG. 3 shows the details of the structure of FIG. 2 according to one embodiment of the invention. The FIG. 3 embodiment, which is a first embodiment 300, includes transducer 302 having electrical pads 304, intermediate elements 306, electrical contacts 308 a and b, which sandwich therebetween an active acoustic element 310, acoustic transducing element 312, acoustic matching element 314, ground sheet 315, optional acoustic window 316, optional filler 318, and optional adhesive 320.

Connector 208 on signal generating and receiving unit 210 of the ultrasound system is coupled to transducer 302. The collection of electrical pads 304 are one embodiment of electrically conducting structure 206. In an embodiment, a two-dimensional array of all electrical pads 304 make up electrically conducting structure 206, and are coupled to intermediate elements 306, which make up intermediate structure 204. Electrical pads 304 can be pure materials, alloys, or any mixture of chromium, nickel, silver, copper, gold, tin, tin oxide, indium and/or indium oxide, or any conductive material, for example. Acoustic transducing element 312 includes electrical contacts 308 a and b, which sandwich therebetween an active acoustic element 310. Active acoustic element 310 can be made with any acoustically active material (i.e., any material capable of converting a sound signal to an electrical signal and visa versa) such as piezoelectric materials such as quartz, lithium niobate, lithium sulfate, ceramic materials, lead zirconate titanate, barium titanate, and lead metaniobate, or other sound generating devices such as micromachined structures. Electrical contacts 308 a and b can be made from materials including, pure materials, alloys, or any mixture of chromium, nickel, silver, copper, gold, tin, tin oxide, indium and/or indium oxide, or any conductive material, for example.

The sandwich of active acoustic element 310 and electrical contacts 308a and b form an acoustic transducing element 312 for generating and/or receiving ultrasound. In the case of a micro-machined device, the sandwich of active acoustic element 310 and electrical contacts 308a and b may be replaced by the micro-machined element and its contacts, which may or may not have a sandwich structure. Acoustic transducing element 312 may also include an acoustic matching element 314 and an optional acoustic window 316. Optional acoustic window 316 may provide electrical isolation protecting a media of interest, such as a patient, from electrical shock. Optionally, acoustic matching element 314 may provide electrical isolation instead of, or in addition to, the electrical isolation provided by optional acoustic window 316. Acoustic matching element 314 may be an assembly of acoustic matching sub-elements. For example, acoustic matching element 314 may have several different layers. Acoustic matching element 314 may be made from materials or mixtures of materials with acoustic matching properties. In an embodiment, acoustic matching element 314 electrically couples electrical contact 308b to ground sheet 315 thereby providing a return to ground. Alternatively, ground sheet 315 need not be included because optional acoustic window 316 can be made from a conductive material and act as a ground sheet. Further, alternatively, electrical contacts 308b may be electrically coupled together forming one sheet, for example, that may be used for a return to ground. In this alternative embodiment, acoustic matching element 314 may or may not be conductive. Joining electrical contacts 308b into one sheet increases the difficulty of acoustically isolating transducers 302. But if the acoustical impedance of the conductive material joining electrical contacts 308b is mismatched, for example, acoustic isolation can be achieved despite the joining material. Optional filler 318 may be placed between intermediate elements 306, completely or partially filling the voids or kerfs (i.e., the spaces between transducers 302). Optional filler 318 may be epoxy resin or other polymers and may include additives to modify filler characteristics. An optional adhesive 320 may be used to secure transducer 302 via electrical pads 304 to connector 208. Optional adhesive 320 may be insulating or conducting adhesives such as epoxy, polyurethane, or silicone with or without various additives for different properties.

Transducers 302 differ from prior art transducers in that they are mounted directly to connector 208 of signal generating and receiving unit 210. Alternatively, structures of intermediate elements 306 that are different from the prior art may also be used.

In another embodiment transducer 302 is mounted on a high density connector (not shown), which is plugged into a corresponding connector 208 of the signal generating and receiving unit 210. The high density connector allows the acoustic transducing element 312 to be positioned further from connector 208. Structures of intermediate elements 306 are further discussed below. Also, the close proximity of transducers 302 to connector 208 may affect the structural, acoustical, and electrical requirements of transducers 302. Consequently, the set of elements that produce optimal performance for transducers 302 may be different than those of similar prior art transducers.

Intermediate elements 306 may serve as posts or columns, and can have a cross section of any shape. For example, the cross section of intermediate elements 306 can be square, rectangular, circular, ovular, triangular, diamond-like, trapezoidal, rhombus-like, or polygonal in shape. Intermediate elements 306 can be a mixture of any of, any combination of, or all of epoxy, polyurethane, and/or silicone, for example. Intermediate elements 306 may also contain heavy particles of any shape or spheres made from material such as tungsten, and may further contain light particles, bubbles, and/or microspheres, which help attenuate sound. The light particles and microspheres can be made from glass and/or plastic, for example. Additionally, intermediate elements 306 may contain graphite or other electrically conductive particles, which also help attenuate sound. Electrically conductive particles could be used as some or all of the heavy and/or light particles, depending on the ranges of density of the conducting particles chosen.

The signal from signal generating and receiving unit 210 is brought through the layers and structures of connector 208 to electrical pads 304 on connector 208's surface. Electrical pads 304, intermediate elements 306, and acoustic transducing elements 312 may be stacked one on top of the other and form the above-mentioned two-dimensional lattice. Acoustic transducing elements 312 may transform the electrical signals to sound waves, or may convert acoustic sound waves to electrical signals. Acoustic transducing elements 312 may be arranged in the same lattice as electrical pads 304, and electrically addressed via signal distribution within signal generating and receiving unit 210.

Intermediate elements 306 form an interconnecting backing media that transmits electrical signals between electrical pads 304, on connector 208 of signal generating and receiving unit 210, and electrical contacts 308 a, on acoustic transducing elements 312. Intermediate elements 306 may have an electrical conductivity that is high enough to minimize signal loss. The signal loss due to the intermediate element 306 is the power loss ($I^2R$, where I is the total current flowing through the array of intermediate elements 306 and R is effective resistance of the array of intermediate elements 306) caused by the resistance of the intermediate element. For example, in an embodiment the conductivity of the intermediate element is adjusted so that the signal loss is kept less than 1 DB.

The total length of the interconnecting media in the direction perpendicular to connector 208 on signal generating and receiving unit 210 and the resistivity of this media are the main factors determining the total resistance of each electrical coupling between acoustic transducing elements 312 and electrical pads 304. Thus, the resistivity of the intermediate elements 306 limit the elements' length, which in turn limits the intermediate structure 204's thickness. Intermediate elements 306 may have adequate acoustical attenuation or impedance to avoid sound reflections from connector 208 of the signal generating and receiving unit 210 that would otherwise reach acoustic transducing elements 312. Intermediate elements 306 may provide mechanical integrity and positioning accuracy of acoustic transducing elements 312 and connector 208 of signal generating and receiving unit 210.

The interconnecting backing media used for intermediate elements 306 may be an electrically anisotropic conducting media that conducts electricity in a direction perpendicular to the surface of the electrical pads 304. The interconnecting backing media may be used to bond acoustic transducing elements 312 to electrical pads 304 on connector 208 of signal generating and receiving unit 210. Intermediate elements 306 may be made from an electrically conductive and acoustically lossy media. An appropriate anisotropic electrical conduction media can be made by incorporating a sparse concentration of conducting elements and/or particles into an electrically insulating medium. The density of the sparse concentration is such that the conducting elements and/or particles do not touch each other in a direction perpendicular to the flow of electrical current due to their low density. The conducting elements and/or particles may have an elongated shape, and the conducting elements are oriented with their longer dimension to reach and make electrical contact on either side of the insulating medium in which they are located. The elements can be whiskers, wires, or arbitrary shapes of conducting media tending to extend the entire length of intermediate element 306. Alternatively, the conducting elements and/or particles may be significantly shorter than and kept relatively parallel to the long direction of intermediate elements 306. The conductive elements should be long enough so that at least a significant number of them tend to touch one another along the length of the particles, but not along the width. The use of an anisotropic conductor reduces the chances of shorting between adjacent intermediate elements 306 when compared to an isotropic conductor.

Alternatively, an isotropic electrically conducting and acoustically appropriate medium may be used to bond the array of acoustic transducing elements 312 to the two-dimensional array of electrical pads 304. Electrical shorts between the intermediate elements 306 can be removed by eliminating the excess media causing the short via mechanical dicing, various ion, electron, plasma, chemical erosion, or other processes.

Optional filler 318 may be an insulator that helps minimize electrical shorting and may have suitable acoustical impedance to prevent crosstalk between transducers 302. It may be desirable to minimize crosstalk by leaving the kerfs near transducers 302 void of filler. Optional filler 318 can be an acoustically attenuating material or a material with a highly mismatched acoustical impedance to transducer 302.

Optional adhesive 320 can be conductive or insulative. If optional adhesive 320 is conductive, it is placed primarily between electrical pads 304 and intermediate element 306. Typically any excess optional adhesive 320 would be removed from the kerfs. However, it is not necessary to remove all of optional adhesive 320 from the kerfs even if it is conductive. The thinner a conductive film the more resistive it is to currents traveling in a plane. Also, the thinner a conductive film the more breaks, or discontinues, it is likely to have in it. Consequently, if any of optional adhesive 320 is conductive and is in the kerfs, the optional adhesive 320 must be thin enough or have enough breaks so that it will act as an insulator in a direction parallel to the surface of connector 208 having electrical pads 304, and the optional adhesive 320 must not cause any shorting.

Similarly, if optional adhesive 320 is insulative, it is placed primarily in the kerfs. Typically, all of optional adhesive 320 on electrical pads 304 is removed. However it is not necessary to remove all of optional adhesive 320 from the electrical pads 304, even if it is insulative. The thinner an insulative film, the more likely it will be able to support a current traveling perpendicular to its surface via arcing, tunneling, or breaks in the insulative film, for example. Consequently, if optional adhesive 320 is insulative, the portion placed on electrical pads 304 must be thin enough or have enough holes in it to allow the flow of a current through it (such as by contact, arcing, or tunneling). Pressure applied while bonding intermediate elements 306 can be used to squeeze excess adhesive out from between the electrical pads 304 and the intermediate elements 306.

In FIGS. 4–10 like components have been given the same alphanumerical labels. To simplify the drawings FIGS. 5–10 show no acoustic matching element 314, ground sheet 315, or optional acoustic window 316, although they are present as in FIGS. 3 and 4. FIGS. 4–10 also share the same ultrasound transducing structure 202 and signal generating and receiving unit 210 as in FIG. 3. FIGS. 5–10 differ from one another primarily in the make up of intermediate structure 204.

Figure 4:
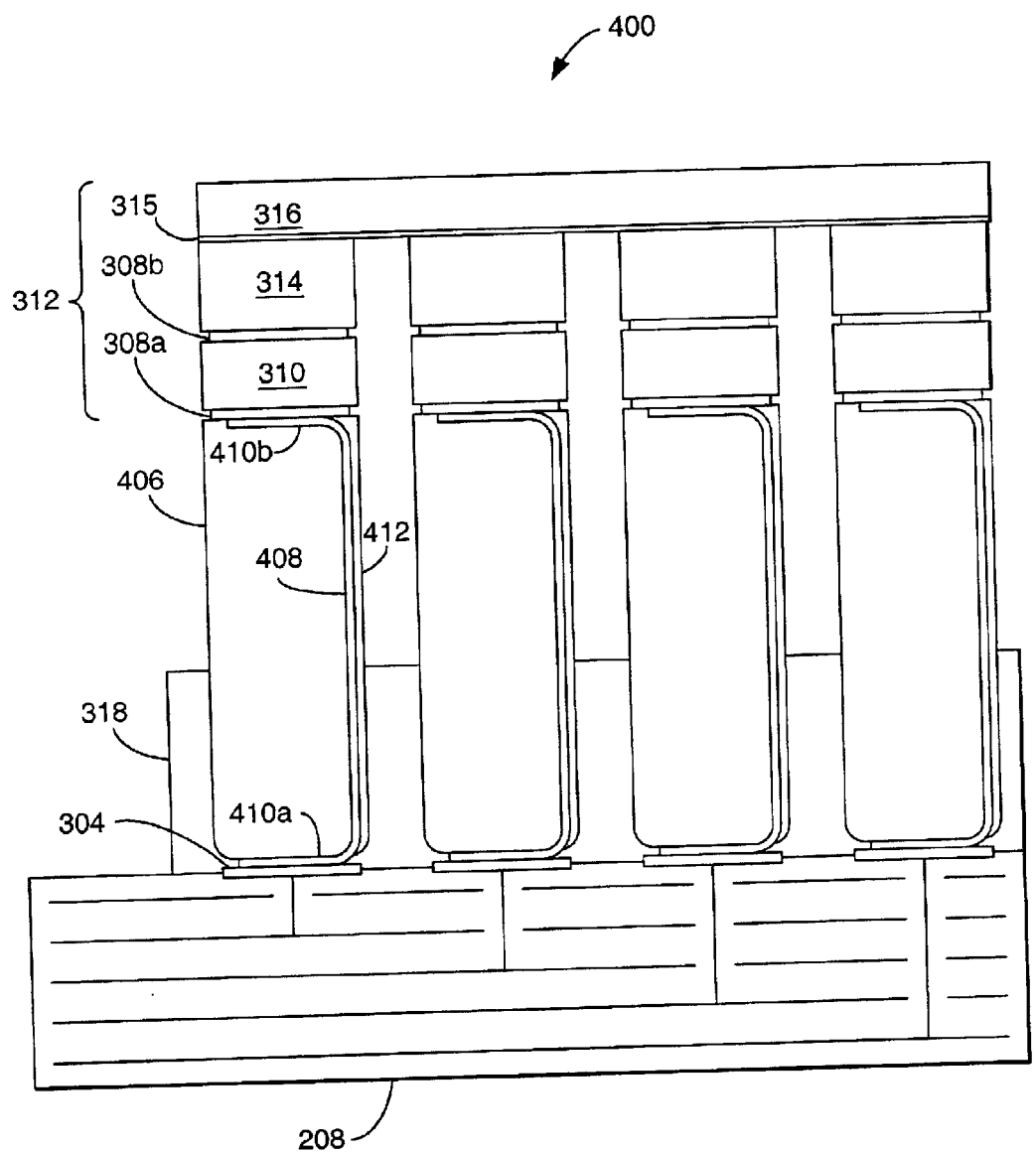
FIG. 4 is an alternative embodiment of the structure of FIG. 2.

FIG. 4 is an alternative embodiment 400 of the structure of FIG. 2. Embodiment 400 has intermediate elements 406, which are insulative and coated with a conductor 408 on any number of sides greater than two, including conductive pads 410a and b located at both ends. Specifically, to explain what is meant by conductor 408 being coated on any number of sides greater than two, conductive pads 410a and b cover intermediate elements 406 on at least part of each of two of its ends. A portion of conductor 408 must also be placed at least partially on a third side of intermediate elements 406 to form an electrical coupling between conductive pads 410a and b. Intermediate elements 406 may be columns or posts made from a mixture of any of, any combination of, or all of, epoxy, polyurethane, and/or silicone containing dense particles or spheres made from material such as, but not limited to, tungsten and bubbles, low density particles, and/or microspheres. The low density particles and microspheres may be made from glass and/or plastic, for example. Conductor 408 may be a thin film that provides electrical interconnection between acoustic transducing elements 312 and electrical pads 304 to which it is bonded or soldered. The conductor 408 may be exposed or covered. If conductor 408 is covered, it may be embedded within, intermediate elements 406 and/or covered by optional film 412. Optional film 412 allows for the removal of any subsequently introduced optional filler 318 by mechanical means, such as dicing wheels, without the danger of damaging conductor 408. Optional film 412 may be a thin film of insulating material or the same material as intermediate elements 406. Conductor 408 may be replaced by conducting wires or whiskers that may be placed along the edges of, or embedded within intermediate elements 406. Optional filler 318 inky encapsulate conductor 408 completely, or partially, as shown in FIG. 4. Optional filler 318 may serve the purposes of providing structural integrity and acoustically isolating individual acoustic transducing elements 312. Optional filler 318 may be of the same material as the posts used for intermediate elements 406 as long as it is insulative, or does not short transducers 302; The higher the electrical conductivity of conductor 408, the lower the signal's loss. In one embodiment, the electrical conductivity provided by conductor 408 may be made high enough to minimize signal loss. The total length of intermediate elements 406 in the direction perpendicular to the signal generating and receiving unit 210, and the per length resistance of conductor 408, will determine the total resistance of the individual couplings between the acoustic transducing elements 312 and electrical pads 304. Due to the relatively high conductivity of metallic films or wires, it is practical to increase the thickness of intermediate structure 204, to position the acoustic array surface to touch the patient in a comfortable way. Intermediate elements 406 may serve as posts or columns and can have a cross section of any shape. Intermediate elements 406 can have essentially the same mechanical and acoustical properties as intermediate elements 306, and therefore may have the same composition, except for the lack of the conducting particles in intermediate elements 406. Because intermediate elements 406 may have a lower resistance, intermediate elements 406 may be made taller than intermediate elements 306. The mechanical properties of intermediate layer 406 may also be slightly different.

Conductor 408 and the bonding material (such as adhesives, solders, and welding material) should not cause acoustic reflections or perturbations. To avoid acoustic reflections or perturbations, the thickness and size of perturbing items within the acoustic path may be small compared to the acoustic wavelengths of interest. Conductor 408 should adhere to the insulating media well enough to retain the structure's mechanical. The insulating media used for intermediate elements 406 should have adequate acoustical attenuation to avoid sound reflections from connector 208 of signal generating and receiving unit 210 that would otherwise reach acoustic transducing element 312. The insulating media used for intermediate elements 406 should have suitable acoustic impedance for optimum performance. The insulating media of intermediate elements 406 may provide mechanical integrity and positioning accuracy of acoustic transducing element 312 and connector 208 of the signal generating and receiving unit 210.

Figure 5:
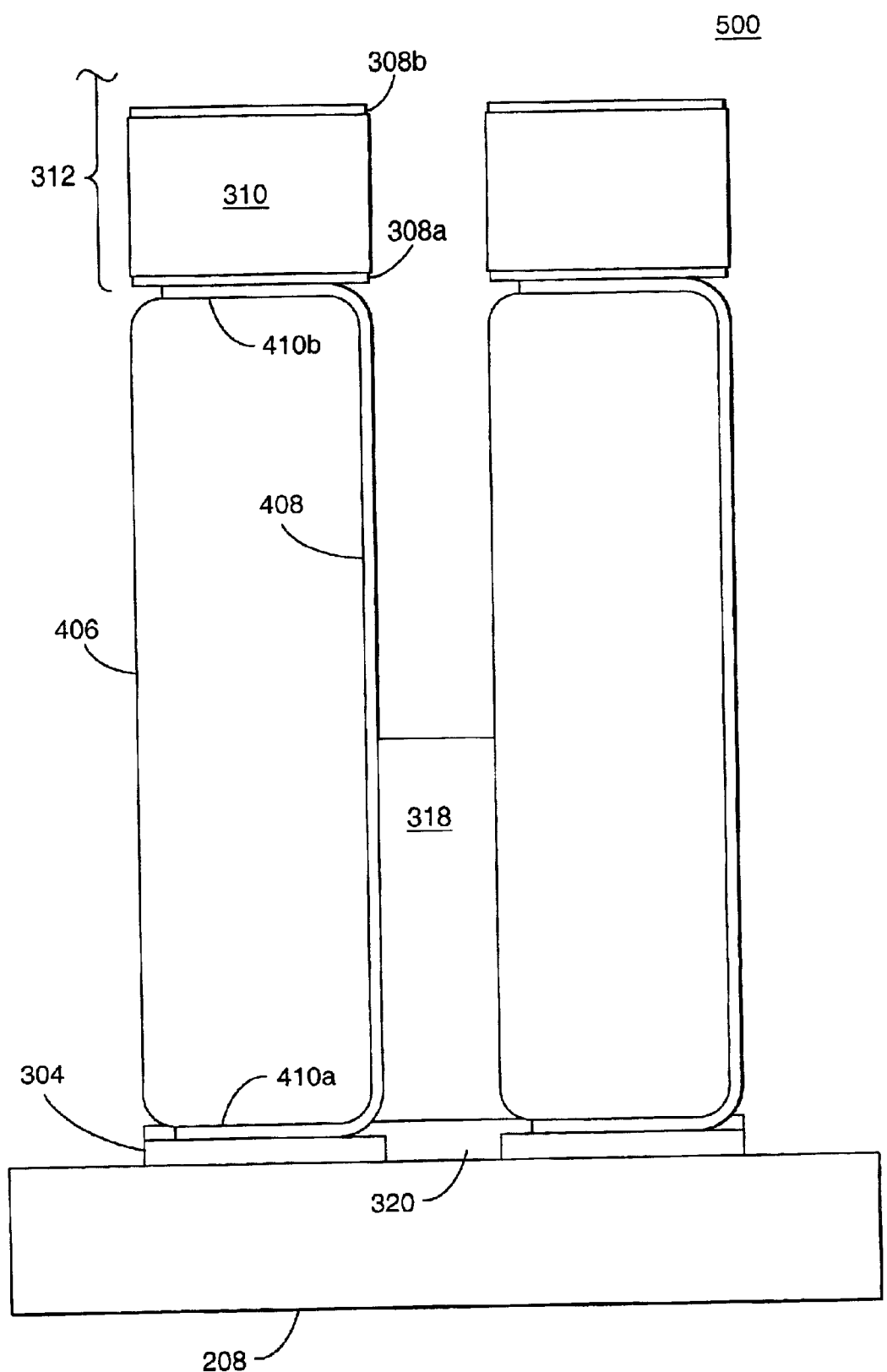
FIG. 5 is a more detailed illustration of FIG. 4.
Figure 6:
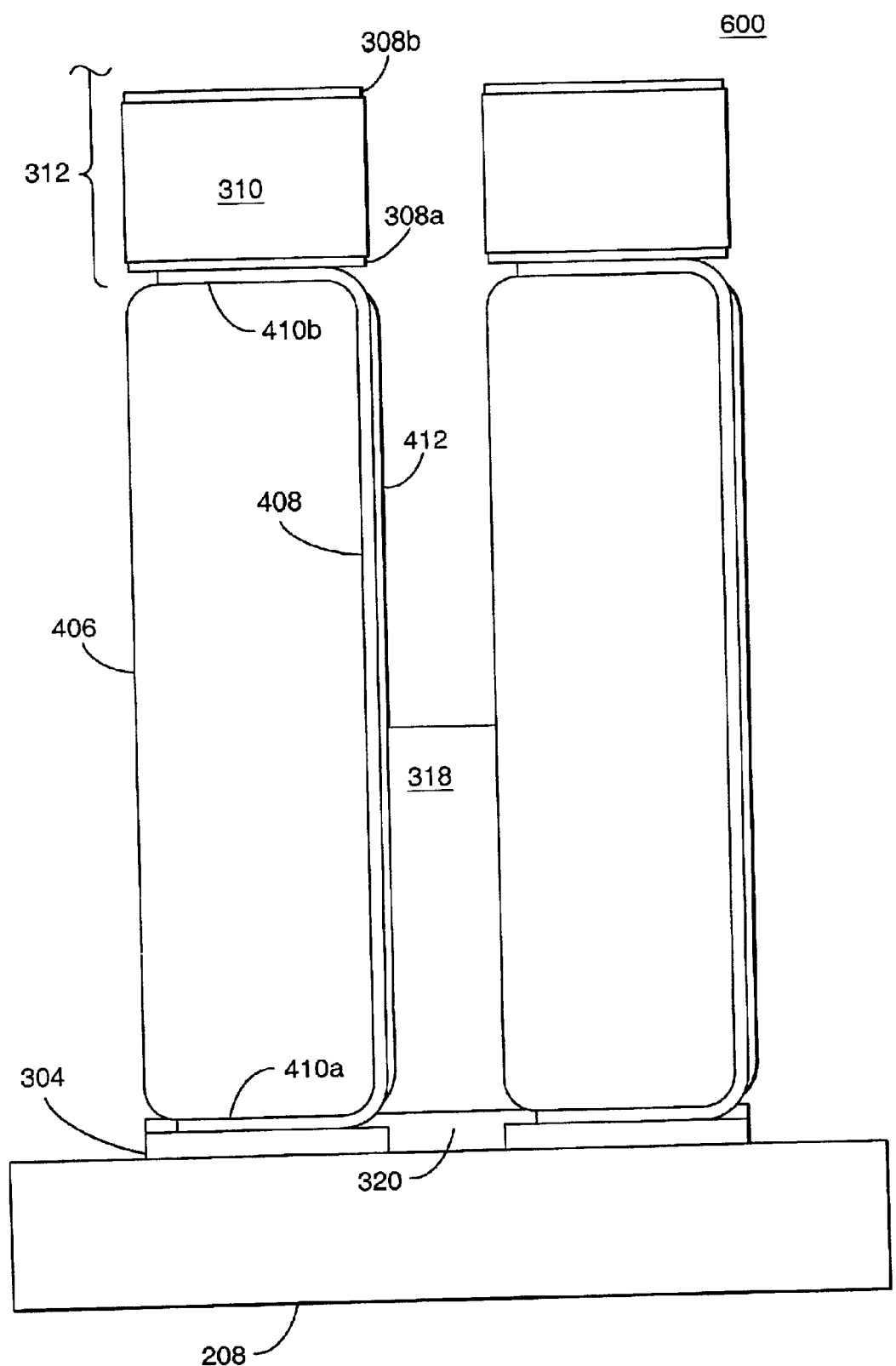
FIG. 6 is another embodiment of the structure of FIG. 2.

FIGS. 5 and 6 are the same as FIG. 4 except that the FIGS. 5 and 6 embodiments include optional adhesive 320. Also, in the FIG. 5 embodiment conductor 408 is exposed, while in the FIG. 6 embodiment, conductor 408 is covered with optional film 412.

Figure 7:
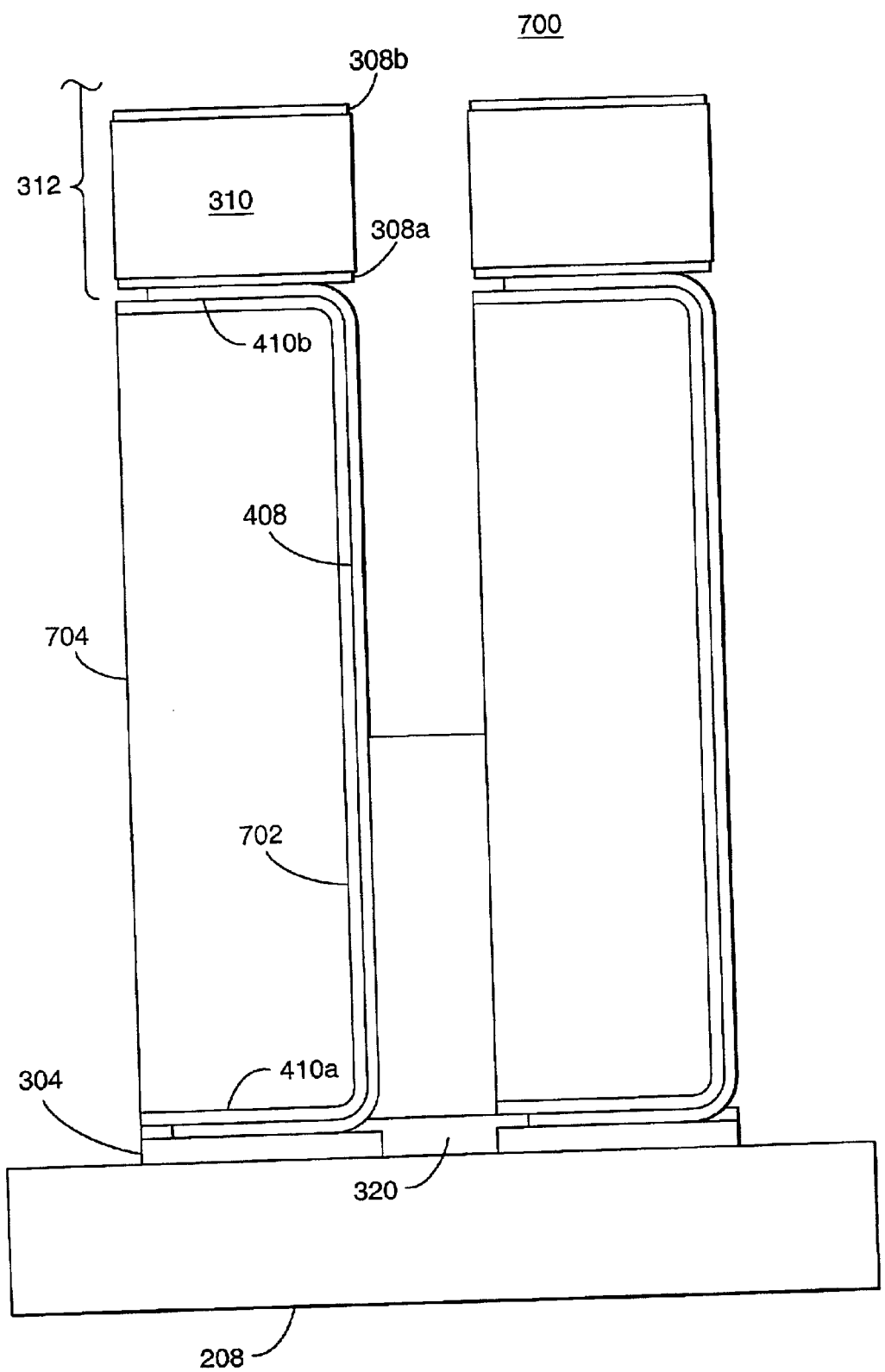
FIG. 7 is another embodiment of the structure of FIG. 2.

FIG. 7 is another embodiment 700 having a coating of an insulative coating 702 made from Kapton™, or Mylar™, for example, on any number of sides greater than two including both ends, and having conductor 408 laminated thereon. The intermediate elements 704 can be the same as intermediate elements 406, or can be a conductor.

Figure 8:
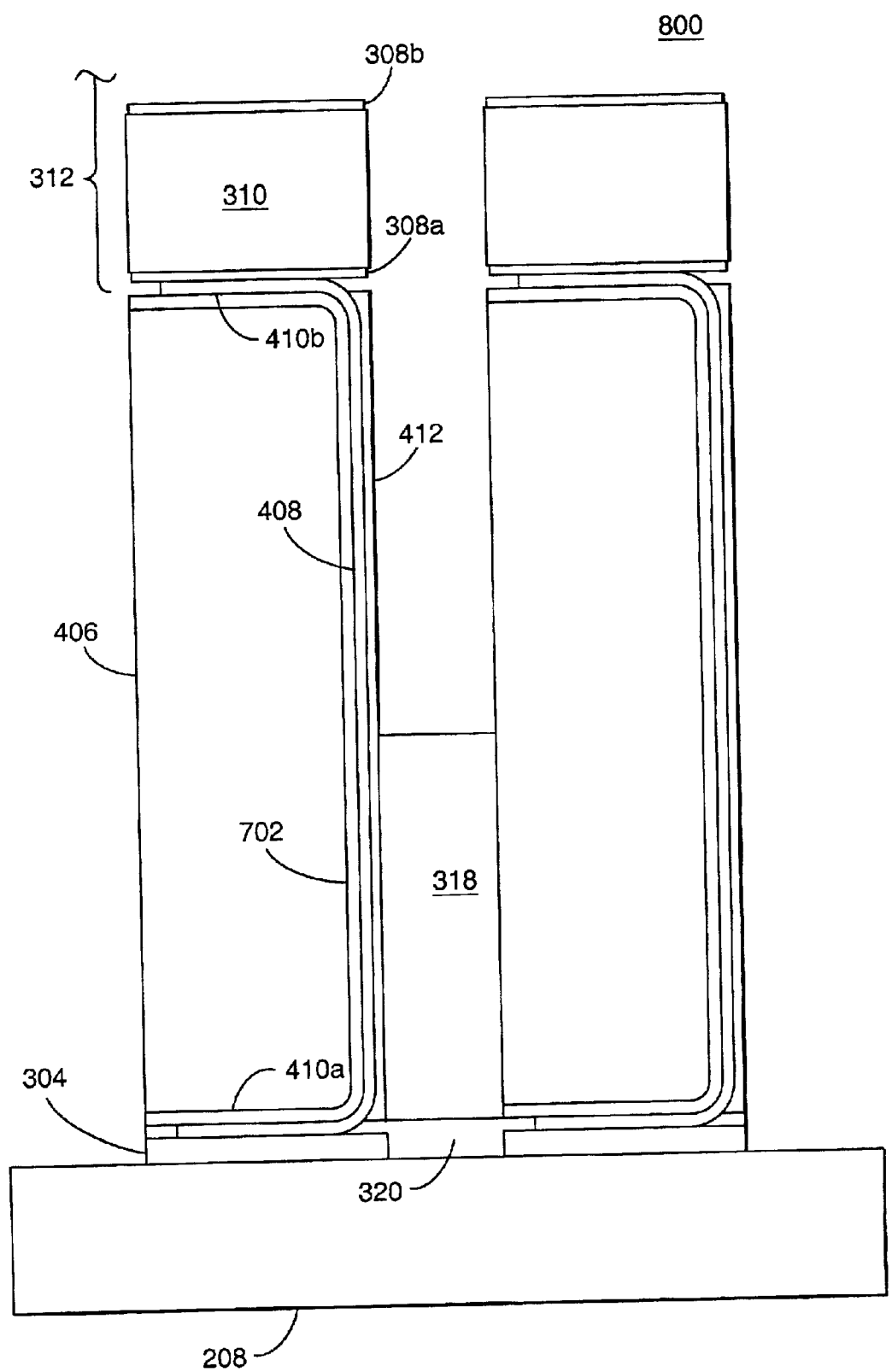
FIG. 8 is another embodiment of the structure of FIG. 2.

FIG. 8 is another embodiment 800, which is the same as that of embodiment 700 of FIG. 7, except that an optional film 412 covers the exposed portion of conductor 408 and is intermediate conductor 408 and optional filler 318.

Although FIGS. 6–8 show optional adhesive 320, it does not need to be present.

Figure 9:
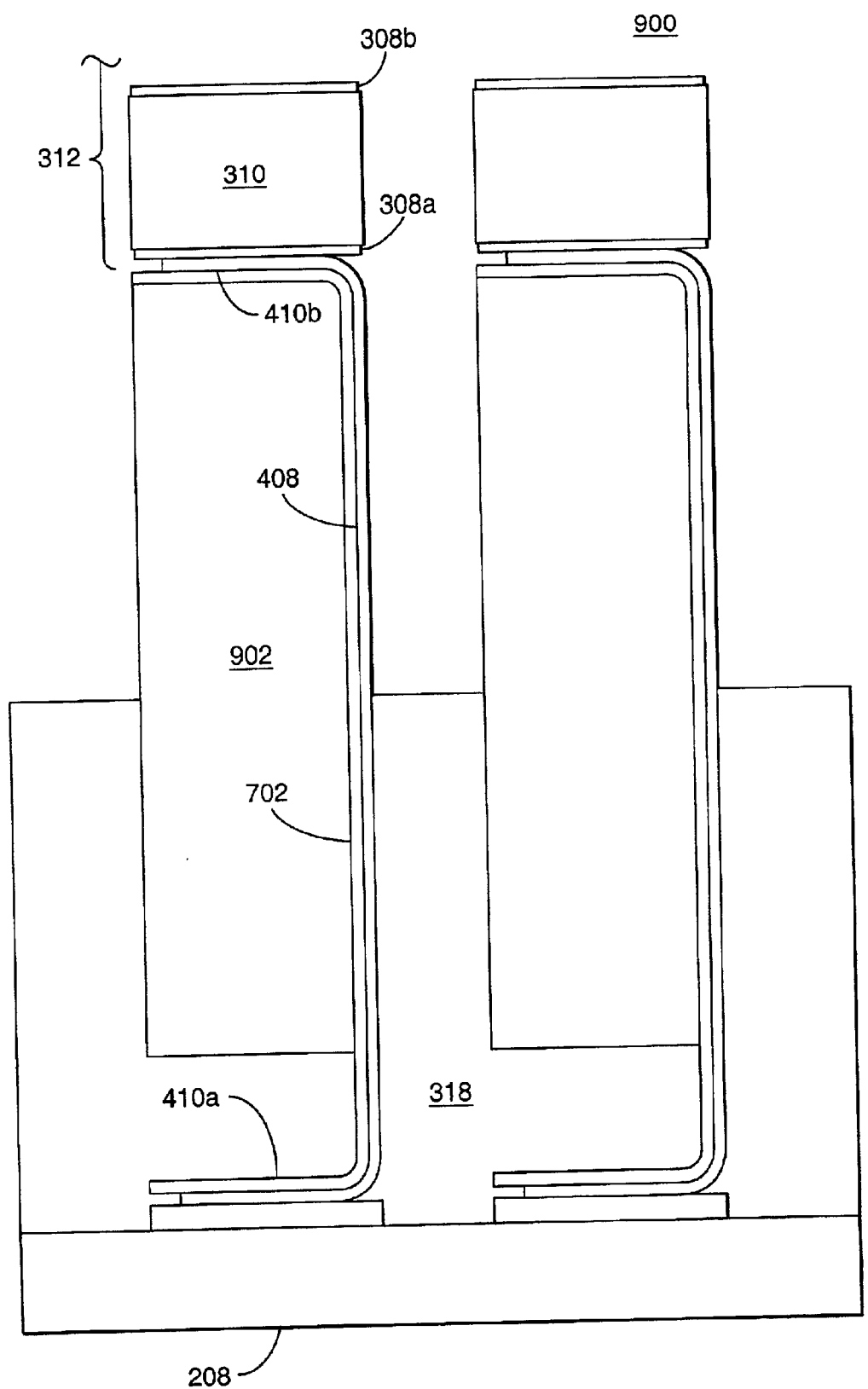
FIG. 9 is another embodiment of the structure of FIG. 2.
Figure 10:
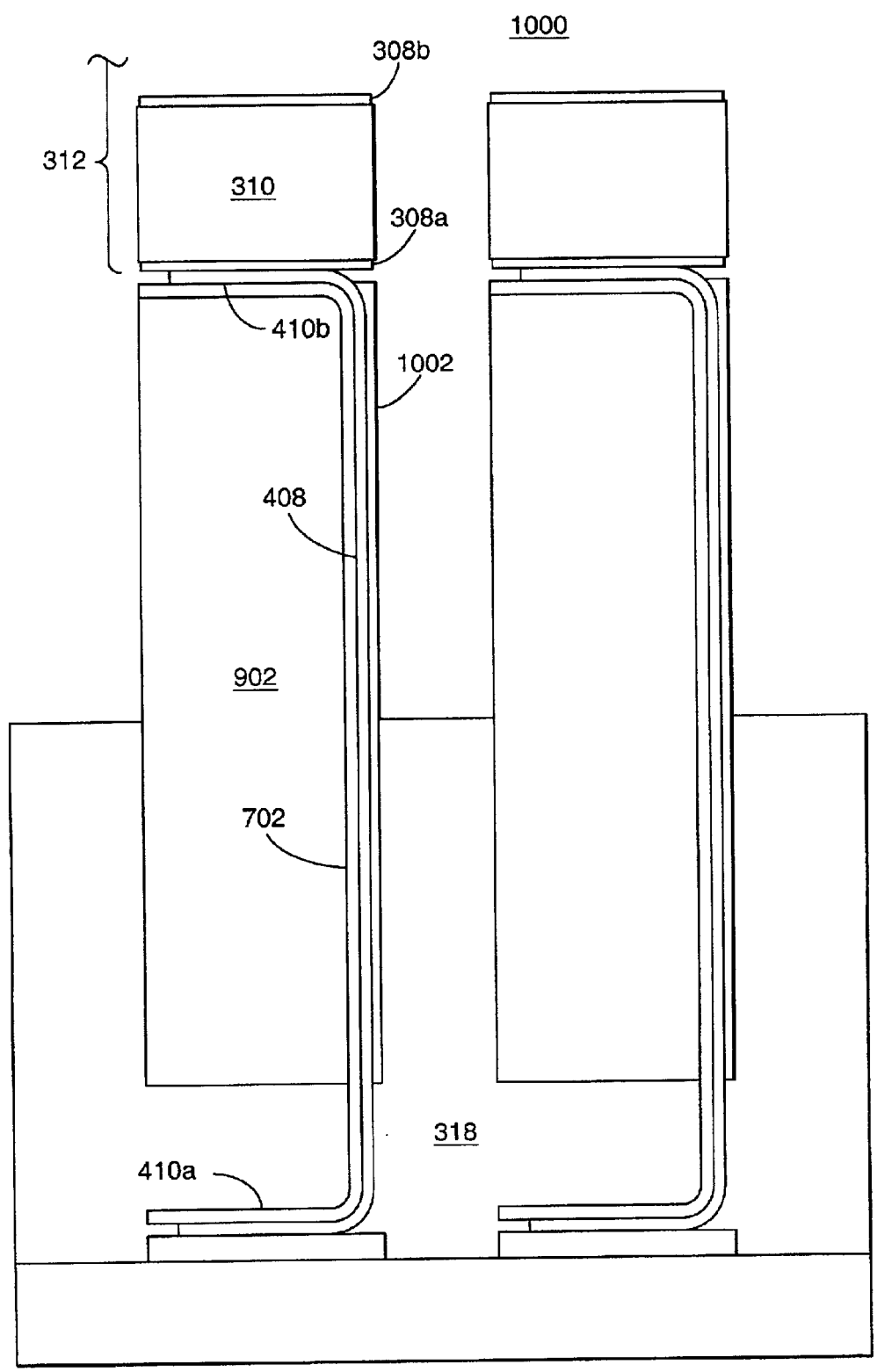
FIG. 10 is another embodiment of the structure of FIG. 2.

FIGS. 9 and 10 are the same as FIGS. 7 and 8, respectively, except that intermediate element 902 and optional film 1002 do not extend all the way down to conductive pads 410 a, leaving a gap. The gap may be filled with optional filler 318. If optional filler 318 is not used, the couplings to electrical pads 304 will remain flexible, thereby providing vibration isolation. If optional filler 318 is used, it provides mechanical integrity and holds the intermediate elements in place. The couplings to the rows and/or columns of electrical pads can be done at any stage of the construction of the interconnection-backing media, or after its completion. Intermediate elements 902 may be posts and can have a cross section of any shape. Intermediate elements 902 can have essentially the same mechanical and acoustical properties as intermediate elements 406 except that since intermediate elements 902 do not extend to conductive pads 410 a, the mechanical properties can be slightly different.

Although FIGS. 9 and 10 do not show optional adhesive 320, it could be included.

Figure 11A:
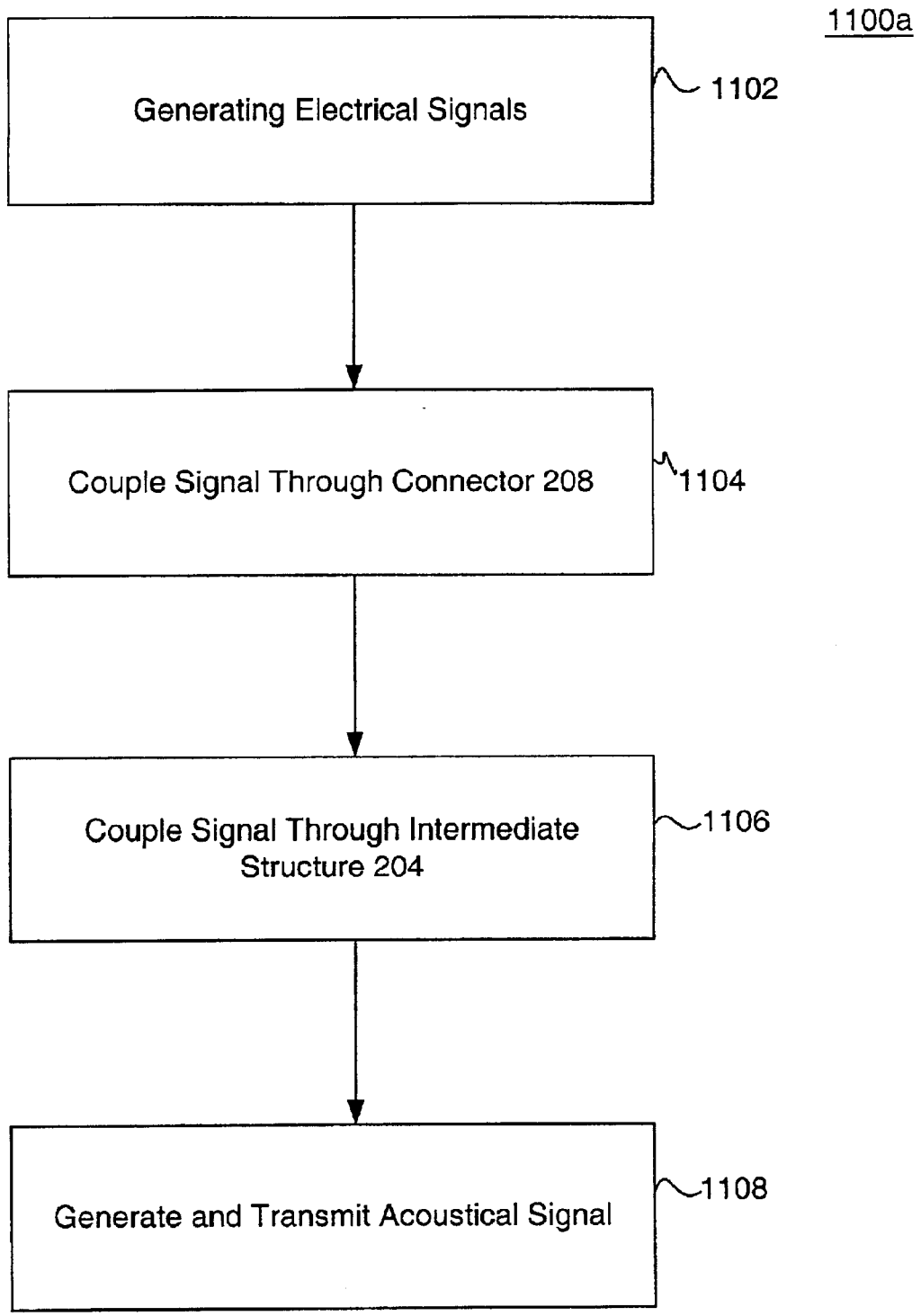
FIG. 11A is a flowchart of a method of transmitting an acoustic signal.

FIGS. 11A and B show flow charts of methods 1100 a and b, respectively, of using an embodiment of the invention. FIG. 11A is a method of transmitting acoustic signals, and FIG. 11B is a method of receiving acoustic signals.

Referring to FIG. 11A, in step 1102 the signal generating and receiving unit 210 generates an electrical signal. In step 1104, the electrical signal is cablelessly coupled via connector 208 and through a possible connector (not shown) and electrical pads 304 to intermediate structure 204. In step 1106, the electrical signal is coupled through intermediate structure 204 to acoustic transducing element 312. In step 1108, acoustic transducing element 312 generates an acoustic signal that is then transmitted via acoustical matching element 314 through optional acoustic window 316.

Figure 11B:
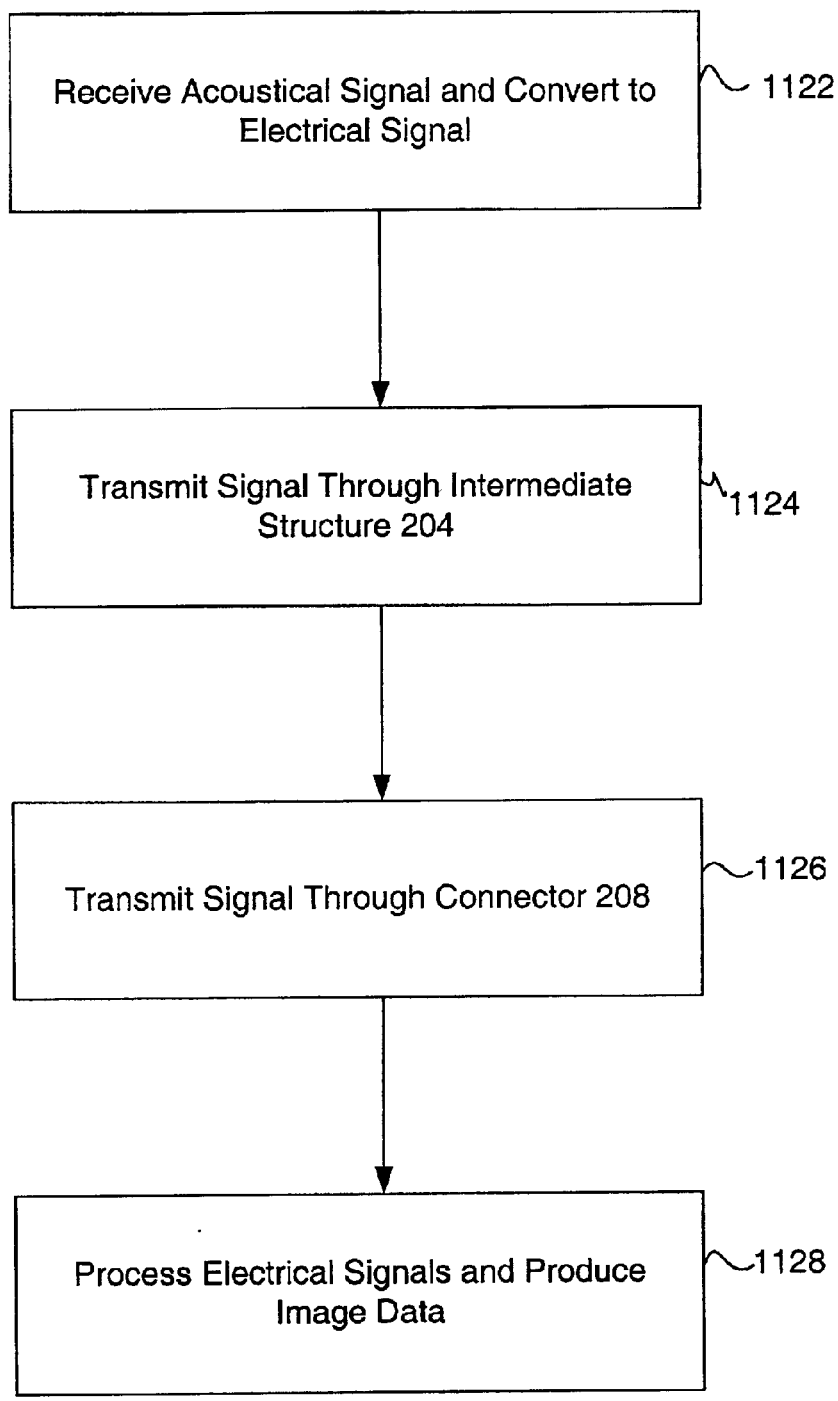
FIG. 11B is a flowchart of a method of receiving an acoustic signal.

Referring to FIG. 11B, the ultrasonic signals from step 1108 (FIG. 11A) are modified (e.g., reflected and/or transmitted) by the media of interest. In step 1122, the modified ultrasonic signals are received. Optionally the reception includes transmitting the ultrasonic signals through the optional acoustical window 316, and receiving them via acoustic matching element 314 by typically a different combination of acoustic transducing elements 312 because the direction of the incident and reflected ultrasound signals is typically different. However, in an embodiment each acoustic transducing element 312 can be used both for receiving and transmitting the modified ultrasonic signal. In another embodiment each acoustic transducing elements 312 may be grouped into pixels having a receiving half and a transmitting half. The acoustic transducing elements 312 convert the ultrasonic signal into an electrical signal. In step 1124, the electrical signals are sent through intermediate structure 204. In step 1126, the signals from intermediate structure 204 are sent via electrically conducting structure 206 through connector 208. In step 1128, the signals from connector 208 are sent back to signal generating and receiving unit 210 for processing to produce an image on a monitor or store as data for producing an image on a monitor. The receiving step may include attenuating reflections within the handheld ultrasound unit 200 such as with the use of optional filler 318 and acoustically the attenuating materials used in intermediate elements 306, 406, and 902.

Figure 12A:
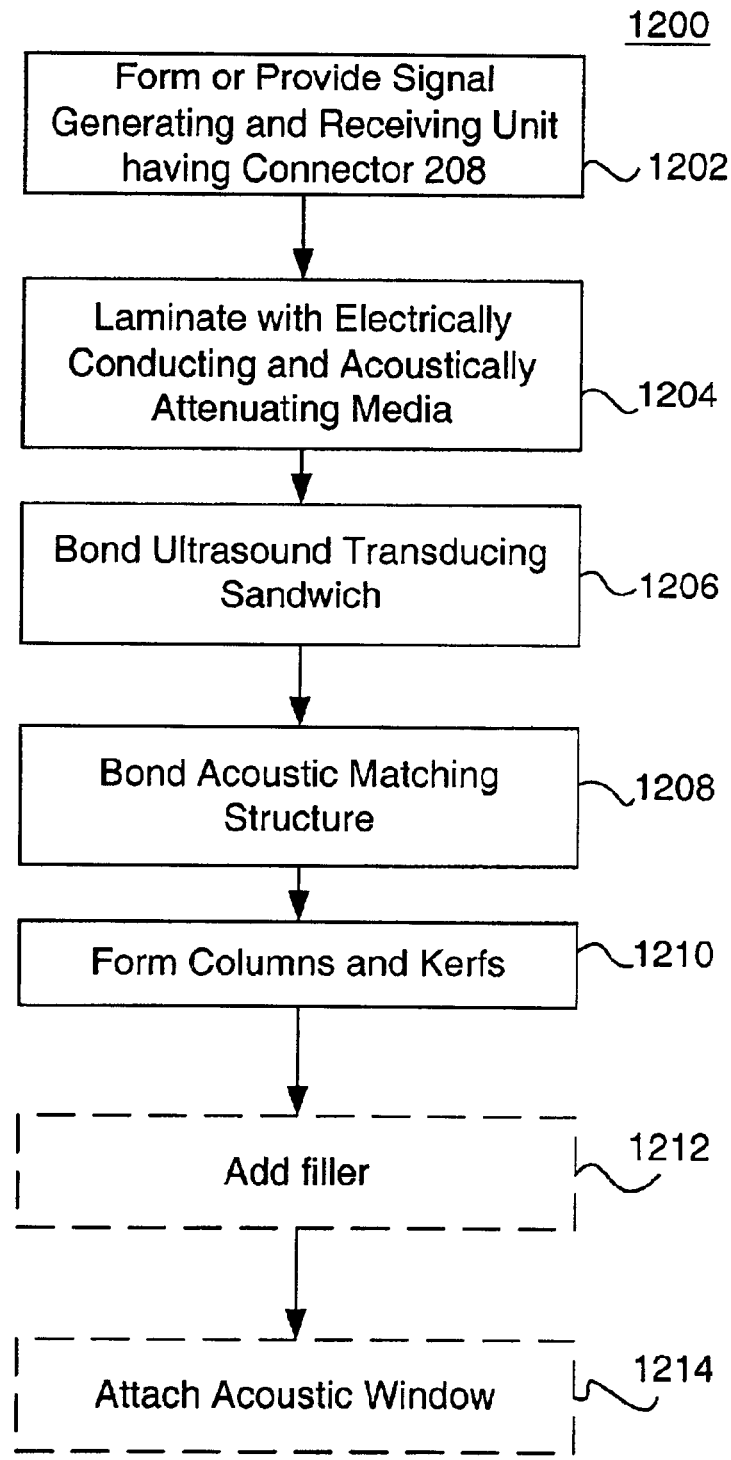
FIG. 12A is a flowchart of a method of making an embodiment of the invention.
Figure 12B:
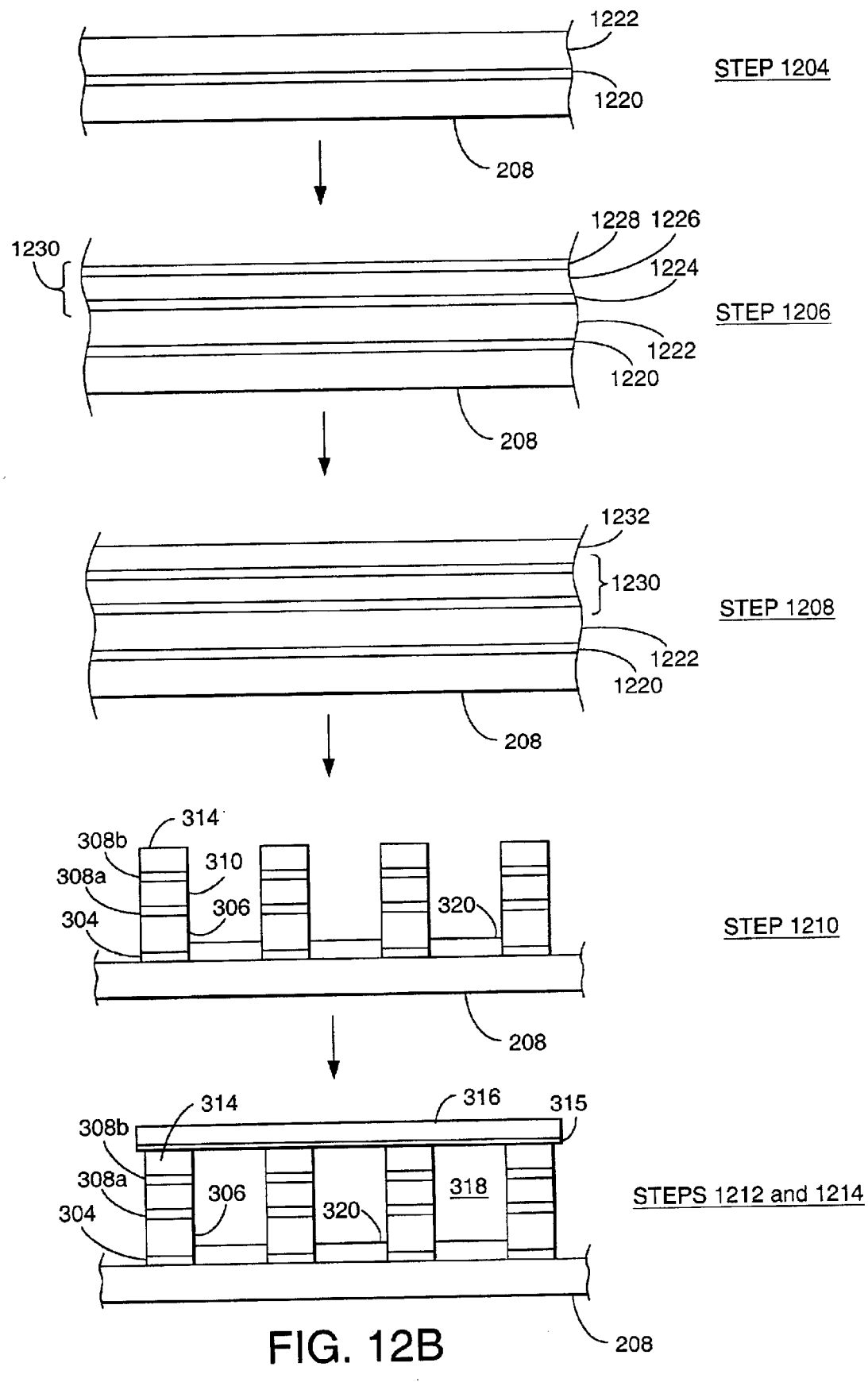
FIG. 12B illustrates the structure at various stages of the method of FIG. 12A.

FIGS. 12A and B show a method 1200 of making an embodiment of the invention, and some of the temporary structures formed at various stages of the process. In step 1202, signal generating and receiving unit is formed or provided, and connector 208 is coupled to or formed on signal generating and receiving unit 210. The rest of signal generating and receiving unit 210 can be formed, assembled, or constructed at anytime relative to forming or coupling connector 208 on signal generating and receiving unit 210. In step 1204 an electrically conductive layer 1220 could be deposited on connector 208 for forming electrical pads 304. Also in step 1204, an electrically conductive and acoustically attenuating media 1222 is laminated on an electrically conductive layer 1220. Further in step 1206, a first conductive layer 1224, an acoustically active layer 1226 and a second conductive layer 1228 form an acoustic transducing sandwich 1230. Acoustic transducing sandwich 1230 is bonded to electrically conductive and acoustically attenuating media 1222. Acoustic transducing sandwich 1230 could be first constructed and then bonded to electrically conductive acoustically attenuating layer 1222, or it could be laminated layer by layer directly upon electrically conductive and acoustically attenuating media 1222. In step 1208, an acoustic matching layer 1232 is bonded to one side of acoustic transducing sandwich 1230. Acoustic matching layer 1232 may include multiple layers and/or have significant structure to improve acoustic matching. In step 1210, material is removed from the composite structure leaving columns and forming the kerfs. A small amount of connector 208 may also be removed during step 1210 in order to be certain that all of the conductive material between electrical pads 304 is removed, and optional adhesive 320 may be added. In step 1212, optional filler 318 is added to the kerfs and allowed to harden. In step 1214, optional acoustic window 316 is bonded to acoustic matching element 314. Optional acoustic window 316 may have ground sheet 315 formed on it by metalization or deposition for example before being secured to acoustic matching element 314.

Figure 13A:
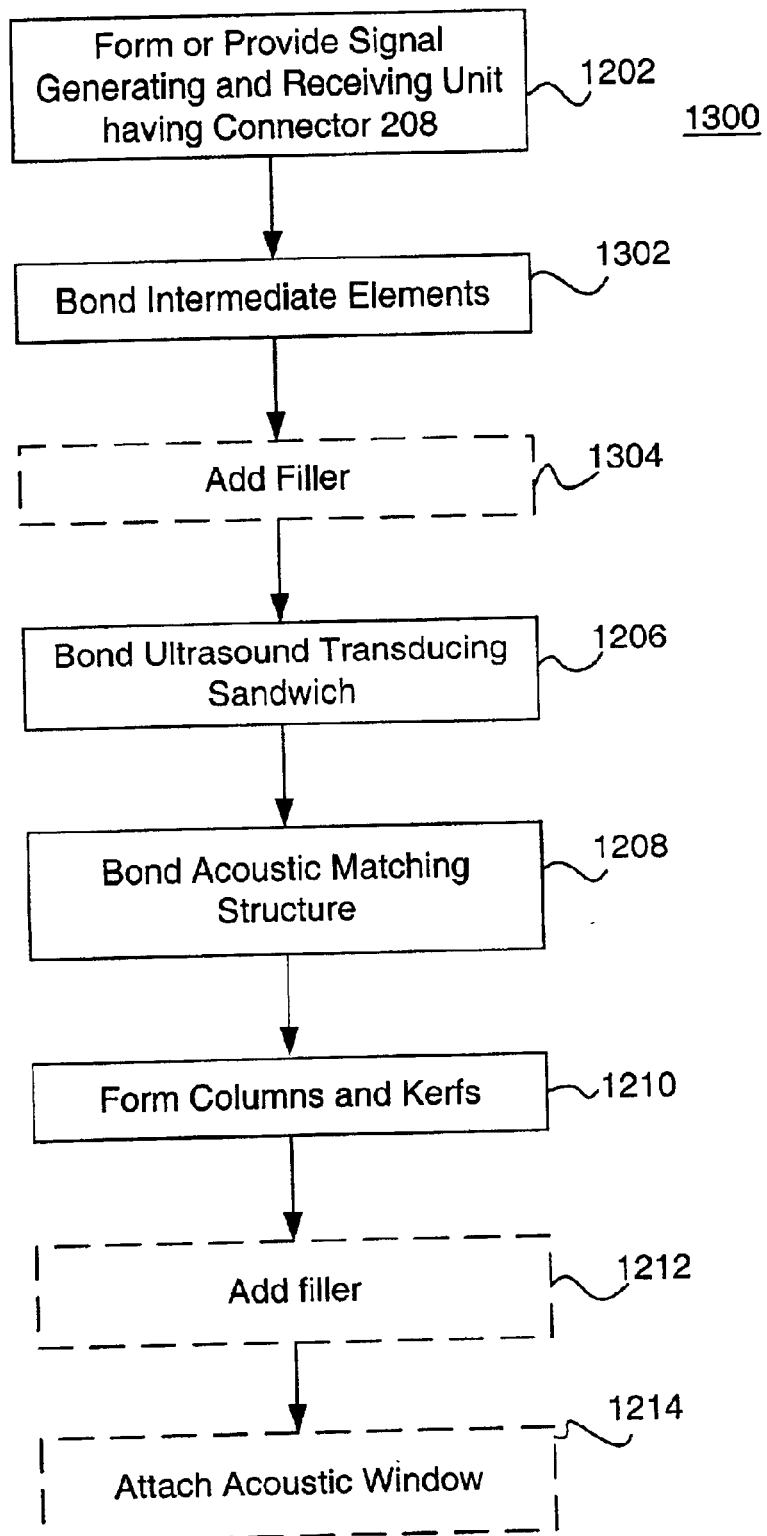
FIG. 13A is a flowchart of a method of making an embodiment of the invention of FIGS. 4–10.
Figure 13B:
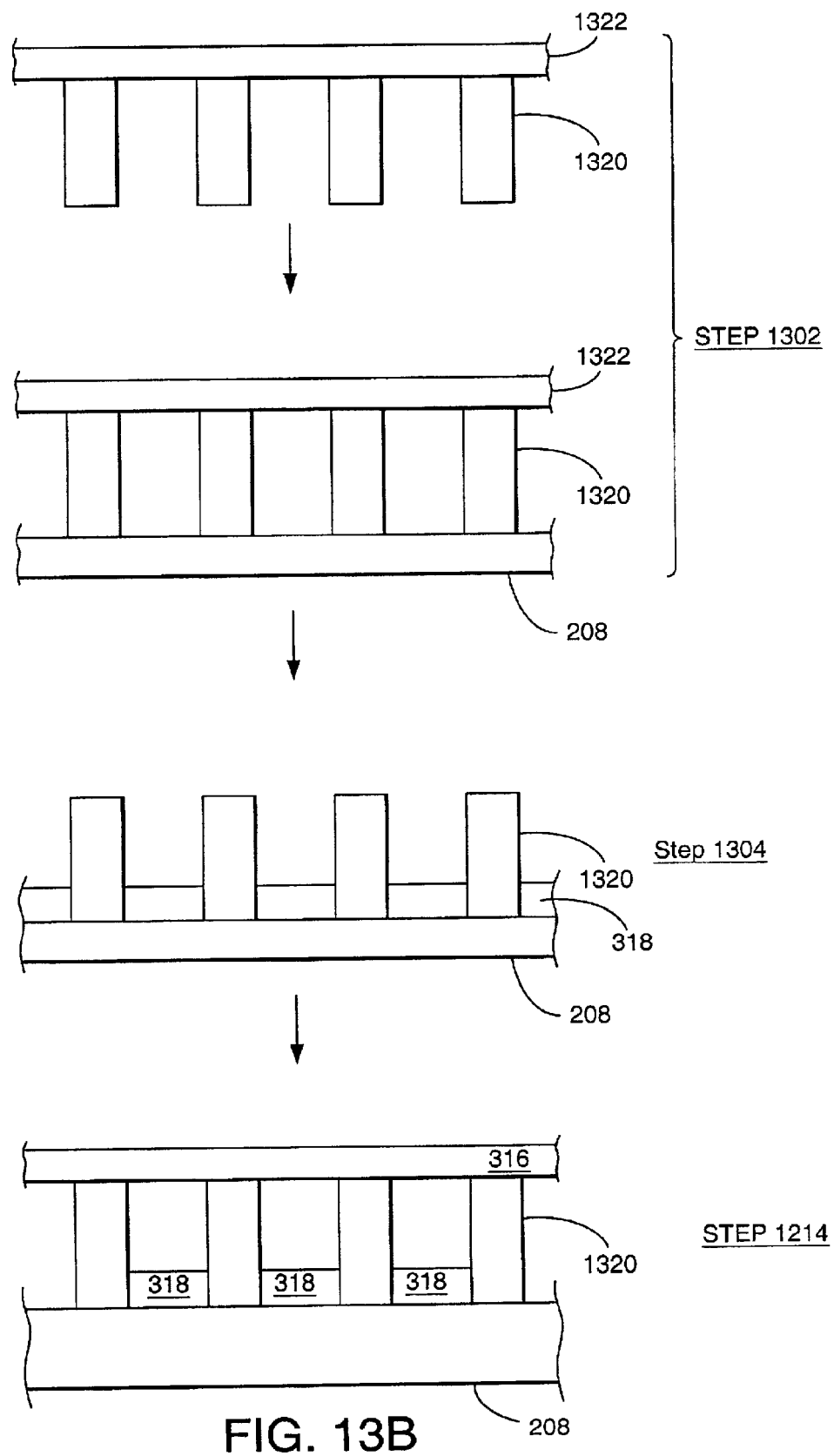
FIG. 13B illustrates the structure at various stages of the method of FIG. 13A.

FIGS. 13A and B show a method 1300 of making an embodiment of the invention and some of the temporary structures formed at various stages of the process. In step 1202, signal generating and receiving unit is formed or provided, and connector 208 is coupled to or formed on signal generating and receiving unit 210, as in method 1200. In step 1302, electrically conductive and acoustically attenuating pillars that form intermediate elements 406 or 902 are attached to connector 208. Although not shown in FIG. 13B, intermediate elements 406 or 902 are formed with conductor 408, optional film 412 or 1002, and insulative coating 702 attached thereto. Although also not shown in FIG. 13B, when intermediate elements 406 or 902 are attached to connector 208, intermediate elements 406 or 902 are bonded to electrical pads 304 on connector 208. Intermediate elements 406 or 902 with conductor 408, optional film 412 or 1002, and insulative coating 702 attached thereto may be formed as structures 1320 on a sheet 1322 so that they can be fixed in positions relative to one another and aligned with electrical pads 304. Structures 1320 may be first formed and then attached to sheet 1322 or may be formed on sheet 1322. The formation of structures 1320 is described in more detail in relation to FIG. 14, below. Alternatively, electrical pads 304 may be included in structures 1320, for example. After bonding structures 1320, to connector 208, sheet 1322 is detached. In optional step 1304, optional filler 318 may be added as a liquid and allowed to harden. In step 1206, an acoustic transducing sandwich is bonded to intermediate structure 204. The acoustic transducing sandwich includes a first conductive film, an acoustically active layer, and a second conductive film. The acoustic transducing sandwich could be first constructed and then bonded to the electrically conductive acoustically attenuating media, or could be laminated layer by layer directly upon the electrically conductive and acoustically attenuating media. Next in step 1206, material is removed from the transducing sandwich to form acoustic transducing elements 312. Alternatively, acoustic transducing elements 312 could also be formed on the same sheet 1322 while making the intermediate elements as part of structures 1320. Method 1300 then proceeds as in method 1200 with steps 1208, 1210, 1212, and 1214. Method 1300 may include neither of or just one of steps 1304 and 1212. Alternatively, part of the optional filler 318 may be added during step 1304 and part may be added during step 1212.

Figure 14:
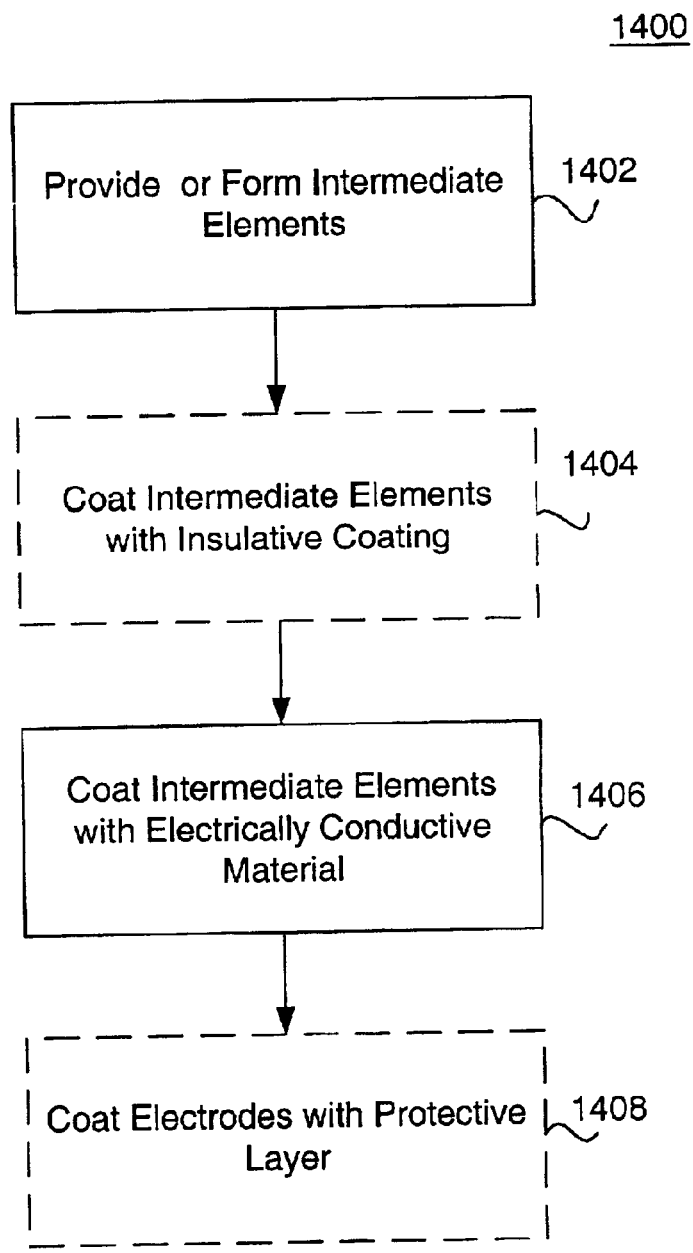
FIG. 14 is a flowchart of a method for making intermediate elements of an embodiment of the invention.

FIG. 14 shows a flowchart of method 1400 for making the intermediate elements of an embodiment of the invention. In step 1402 method 1400 starts with providing or forming intermediate elements 406 or 902, which may be formed on sheet 1322 or formed separately and then attached to sheet 1322 after the completion of method 1400. If structures 1320 (which form intermediate elements 406 or 902) are formed on sheet 1322 a conductive layer (not shown) is first be deposited on sheet 1322 and then an insulative layer (not shown) is deposited from the composite structure leaving columns to form conductive pads 410b attached to intermediate elements 406 or 902. Conductive pads 410b form a first part of conductor 408. Some material from sheet 1322 may also be removed or alternatively the conductive layer (not shown) may be left exposed and not separated into conductive pads 410 b. Optionally, in step 1404, intermediate elements 406 are coated with an insulative coating 702 some of which may be removed to expose the conductive layer (not shown) or conductive pads 410b. In step 1406, intermediate elements 406 are coated with conductor 408. However, if structures 1320 were formed on sheet 1322 then the part of conductor 408 that forms conductive pad 410b will already be present. The conductor 408 may be attached to insulating coating 702 or embedded within insulating coating 702 first and then attached to intermediate elements 406 via insulative coating 702. The conductive layer (not shown) is separated into conductive pads 410b if not already separated in step 1402. In optional step 1408, the conductor 408 is covered with optional film 412 or 1002. Optional film 412 or 1002 provides an insulating and protective coating thereby embedding conductor 408 in the composite structure formed by intermediate elements 406 or 902 and optional film 412 or 1002, respectively.

Although the word "structure" is used to describe many elements, these elements could also be assemblies, which in this Application is generic to the word "structure" but also includes assembles or collections of parts. The word "coupling" in this application is generic to direct connection and a connection made via an intermediate element as well as any other type of coupling, link or way of attaching elements together.

The invention could also be constructed using other signals, such as optical signals rather than electrical signals. In an optical embodiment electrically conducting structure 206 may be replaced with an optical connection, for example. Although the acoustic transducing elements 312 are depicted as having electrical contacts 308a and b, they are only necessary if electrical energy is used to excite the active acoustic elements 310. If the active acoustic elements 310 are excited by other forms of energy such as by using electric magnetic waves or mechanical energy, the electrical contacts 308a and b may not be used or may be replaced by coupling contacts for securing the active acoustic element in place.

Although the invention has been described with reference to specific embodiments, it will be understood by those skilled in the art that various changes may be made and equivalents may be substituted for elements thereof without departing from the true spirit and scope of the invention. In addition, modifications may be made without departing from the essential teachings of the invention.

What is claimed is:

1. An ultrasound system comprising:
   a signal generating and receiving unit;
   a cableless coupling assembly, the cableless coupling assembly comprising intermediate elements coupled to electrical pads wherein the intermediate elements comprise electrically conductive particles, and is configured to attenuate sound; and
   an ultrasound transducing assembly coupled via the cableless coupling assembly to the signal generating and receiving unit wherein the ultrasound transducing assembly comprises:
      at least one transducer configured to provide sufficient bandwidth for multiple frequency operation, the at least one transducer configured to be electrically matched to the signal generating and receiving unit.

2. An ultrasound system comprising:
   at least one transducer configured to provide sufficient bandwidth for multiple frequency operation, the transducer comprising:
      acoustic transducing elements; and
      an acoustically isolating assembly connected to the acoustic transducing elements; and
   a signal generating and receiving unit connected to the acoustically isolating assembly wherein the transducers are directly connected to the signal generating and receiving unit via a cableless connector and the signal generating and receiving unit is electrically matched to the at least one transducer.

3. The system of claim 2 wherein the acoustic transducing elements include at least an acoustically active material between two electrical contacts.

4. The system of claim 3 wherein the acoustic transducing elements include an acoustic matching assembly coupled to one of the two electrical contacts and an acoustic window coupled to the acoustic matching assembly.

5. The system of claim 2 wherein the signal generating and receiving unit includes a motherboard.

6. The system of claim 2 wherein a filler material is placed within kerfs formed by the acoustically isolating assembly.

7. The system of claim 2 wherein the acoustically isolating assembly includes posts of an electrically conductive and acoustically attenuating material.

8. The system of claim 7 wherein the posts are anisotropic conductors.

9. The system of claim 7 wherein the posts are isotropic conductors.

10. The system of claim 2 wherein the acoustically isolating assembly includes insulating posts having conductors for conducting electrical signals.

11. The system of claim 10 wherein the conductors are partially embedded within the posts.

12. The system of claim 10 wherein the conductors are attached to the outside of the posts.

13. The system of claim 10 wherein the conductors have an insulative backing that is coupled with the posts.

14. The system of claim 10 wherein the conductors are longer than and extend beyond the posts.

15. An ultrasound system comprising:
   circuitry having a signal generating and receiving unit;
   acoustic transducing elements configured to provide sufficient bandwidth for multiple frequency operation, and electrically matched to the circuitry, the acoustic transducing elements comprising:
      an acoustically active material between two electrical contacts;
      an acoustic matching assembly coupled to one of the two electrical contacts; and
      an acoustic window coupled to the acoustic matching assembly;
   a cableless coupling assembly coupled to the signal generating and receiving unit and the acoustic transducing elements wherein a transducer is directly connected to the signal generating and receiving unit via a connector, the cableless coupling assembly comprising:
      an acoustically isolating assembly having posts configured to be electrically conductive and acoustically attenuating, isolating the acoustic transducing elements; and
      a filler material placed within kerfs formed by the acoustically isolating assembly.

16. The system of claim 15 wherein the posts are anisotropic conductors.

17. The system of claim 15 wherein the posts are isotropic conductors.

18. The system of claim 15 wherein the acoustically isolating assembly includes conductors for conducting electrical signals coupled to the posts.

19. The system of claim 18 wherein the conductors are partially embedded within the posts.

20. The system of claim 18 further comprising an acoustical index matching element.

21. The system of claim 18 wherein the conductors are attached to the outside of the posts.

22. The system of claim 18 wherein the conductors have an insulative backing that is coupled with the posts.

23. The system of claim 18 wherein the conductors are longer than and extend beyond the posts.

24. An ultrasound system comprising:
   signal generating and receiving means;
   ultrasound transducing means configured to provide sufficient bandwidth for multiple frequency operation, and electrically matched to the signal generating and receiving means;
   cableless coupling means connected to the signal generating and receiving means and to the ultrasound transducing means wherein the ultrasound transducing means are directly connected to the signal generating and receiving means via connection means, including
      means for acoustically isolating the ultrasound transducing means from the signal generating and receiving means, and
      means for conducting electricity; and
   acoustic backing means for attenuating acoustic reflections.

* * * * *